United States Patent [19]

Kohn et al.

[11] Patent Number: 5,705,514

[45] Date of Patent: *Jan. 6, 1998

[54] SIGNAL TRANSDUCTION INHIBITOR COMPOUNDS

[75] Inventors: Elise C. Kohn, Olney; Lance A. Liotta, Potomac; Christian C. Felder, Bethesda, all of Md.

[73] Assignee: The United States of America as represented by the Department of Health and Human Services, Washington, D.C.

[*] Notice: The term of this patent shall not extend beyond the expiration date of Pat. No. 5,132,315.

[21] Appl. No.: 455,825

[22] Filed: May 31, 1995

Related U.S. Application Data

[62] Division of Ser. No. 270,181, Jul. 1, 1994, Pat. No. 5,482,954, which is a division of Ser. No. 985,402, Dec. 4, 1992, Pat. No. 5,359,078, which is a continuation-in-part of Ser. No. 355,744, May 19, 1989, Pat. No. 5,132,315, which is a continuation-in-part of Ser. No. 944,009, Sep. 11, 1992, abandoned, which is a continuation of Ser. No. 637,145, Jan. 3, 1991, abandoned, and a continuation-in-part of Ser. No. 894,891, Jun. 8, 1992, abandoned.

[51] Int. Cl.$^6$ .................... A61K 31/41; A61K 31/415
[52] U.S. Cl. .................... 514/359; 514/383; 514/396; 514/398; 514/399; 548/255; 548/265.4; 548/265.8; 548/335.5; 548/343.5
[58] Field of Search .................... 514/359, 383, 514/396, 398, 399; 548/255, 265.4, 265.8, 326.5, 335.5, 343.5

[56] References Cited

U.S. PATENT DOCUMENTS

| | | | |
|---|---|---|---|
| 4,299,834 | 11/1981 | Austel et al. | 514/264 |
| 4,590,201 | 5/1986 | Bochis et al. | 514/359 |
| 4,659,720 | 4/1987 | Chabala et al. | 514/313 |
| 4,816,469 | 3/1989 | Bochis et al. | 514/359 |
| 4,847,257 | 7/1989 | Hupe et al. | 514/269 |
| 5,045,543 | 9/1991 | Hupe | 514/359 |
| 5,132,315 | 7/1992 | Kohn et al. | 514/359 |

FOREIGN PATENT DOCUMENTS

| | | |
|---|---|---|
| 0 114 347 | 8/1984 | European Pat. Off. |
| 0 151 528 | 8/1985 | European Pat. Off. |
| 0 229 011 | 7/1987 | European Pat. Off. |
| 0 288 431 | 10/1988 | European Pat. Off. |
| 59-62593 | 4/1984 | Japan |

OTHER PUBLICATIONS

Lovelette, C.A., et al. "Studies in Nonbridgehead Fused Nitrogen Heterocycles. Fused 1,2,3–Triazoles", *J. Org. Chem.*, vol. 37, No. 25, pp. 4124–4128, 1972.

Hamilton, Thomas C., et al., "Characterization of a Xenograft Model of Human Ovarian Cancer Which Produces Ascites and Intraabdominal Carcinomatosis in Mice", *Cancer Research*, vol. 44, pp. 5286–5290, 1984.

Allen, Lee F., et al. "G–protein–coupled receptor genes as protooncogenes: Constitutively activating mutation of the $\alpha_{1B}$–adrenergic receptor enhances mitogenesis and tumorigenicity", *Proc. Natl. Acad. Sci. USA*, vol. 88, pp. 11354–11358, 1991.

Julius, David, et al., "Ectopic Expression of the Serotonin 1c Receptor and the Triggering of Malignant Transformation", *Science*, vol. 244, pp. 1057–1062, 1989.

Jelsema, Carole L., et al., "Stimulation of phospholipase $A_2$ activity in bovine rod outer segments by the $\beta\gamma$ subunits of transducin and its inhibition by the a subunit", *Proc. Natl. Acad. Sci. USA*, vol. 84, pp. 3623–3627, 1987.

Liotta, Lance, A., et al., "Tumor cell autocrine motility factor", *Proc. Natl. Acad. Sci. USA*, vol. 83, pp. 3302–3306, 1986.

Gutkind, J. Silvio, "Muscarinic acetylcholine receptor subtypes as agonist–dependent oncogenes", *Proc. Natl. Acad. Sci. USA*, vol. 88, pp. 4703–4707, 1991.

(List continued on next page.)

*Primary Examiner*—Yogendra N. Gupta
*Attorney, Agent, or Firm*—Townsend and Townsend and Crew

[57] ABSTRACT

A method of inhibiting the invasion and metastasis of malignant solid tumors in mammals, said method comprising administering to said mammal an anti-proliferative, anti-invasive and anti-metastasis effective amount of a compound selected from the group of formulas consisting of:

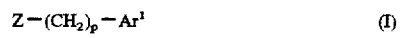

and

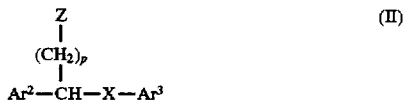

wherein:

p is an integer of from 0 to 4;

$Ar^1$ is a moiety selected from the group consisting of —$Ar^2$—X—$Ar^3$, phenyl, trioxaadamantyl, anthracenyl, anthraquinonyl, naphthyl, phenanthryl, and substituted versions thereof;

$Ar^2$ and $Ar^3$ are each aromatic moieties independently selected from the group consisting of phenyl, naphthyl, and substituted versions thereof;

X is a linking moiety selected from the group consisting of O, S, $SO_2$2, CO, CHCN, straight chain alkyl, alkoxy, and alkoxyalkyl; and Z is a nitrogen-containing heterocyclic moiety selected from the group consisting of imidazolyl, 1,2,3-triazolyl, 1,2,4-triazolyl and substituted versions thereof, said heterocyclic moieties being attached to the —$(CH_2)_p$— portion of the molecule at the N1 position of the heterocycle.

14 Claims, 13 Drawing Sheets

OTHER PUBLICATIONS

Landis, Claudia, A., et al., "GTPase inhibiting mutations activate the α chain of $G_S$ and stimulate adenylyl cyclase in human pituitary tumours", *Nature*, vol. 340, pp. 692–696, 1989.

Fleischman, Laurie, F., et al., "Ras-Transformed Cells: Altered Levels of Phosphatidylinositol-4,5-bisphosphate and Catabolites", *Science*, vol. 231, pp. 407–410, 1986.

Alonso, Teresa, et al., "Malignant transformation by ras and other oncogenes produces common alterations in inositol phospholipid signaling pathways", *Proc. Natl. Acad. Sci. USA*, vol. 85, pp. 4271–4275, 1988.

Pozzatti, R., et al., "Primary Rat Embryo Cells Transformed by One or Two Oncogenes Show Different Metastatic Potentials", *Science*, vol. 232, pp. 223–227, 1986.

Jackowski, Suzanne, et al., "A Guanine Nucleotide–dependent Phosphatidylinositol 4,5–Disphosphate Phospholipase C in Cells Transformed by the v–fms and v–fes Oncogenes", *The Journal of Biological Chemistry*, vol. 261, No. 11, pp. 4978–4985, 1986.

Church, Jon G., "G–protein–mediated Epiderma Growth Factor Signal Transduction in a Human Breast Cancer Cell Line", *The Journal of Biological Chemistry*, vol. 263, pp. 4242–4246, 1988.

Ashkenazi, Avi, et al., "Acetylcholine analogue stimulates DNA synthesis in brain–derived cells via specific muscarinic receptor subtypes", *Letters to Nature*, pp. 146–150, 1989.

Young, Dallan, et al., "Isolation and Characterization of a New Cellular Oncogene Encoding a Protein with Multiple Potential Transmembrane Domains", *Cell*, vol. 45, pp. 711–719, 1986.

Kohn, Elise, C., et al., "In Vivo Efficacy of a Novel Inhibitor of Selected Signal Transduction Pathways Including Calcium, Arachidonate, and Inositol Phosphates", *Cancer Research*, vol. 52, pp. 3208–3212, 1992.

Stracke, Mary, L., et al., "Pertussis Toxin Inhibits Stimulated Motility Independently of the Adenylate Cyclase Pathway in Human Melanoma Cells", *Biochemical and Biophysical Research Communications*, vol. 146, No. 1, pp. 339–345, 1987.

Allende, Jorge, E., "GTP–mediated macromolecular interactions: the common features of different systems", pp. 2356–2367, 1988.

Neer, Eva J., et al., "Roles of G Protein subunits in transmembrane signaling", *Nature*, vol. 333, pp. 129–134, 1988.

Berridge, Michael, J., et al., "Inositol Trisphosphate and Diacylglycerol: Two Interacting Second Messengers", *Ann. Rev. Biochem.*, vol. 56, pp. 159–193, 1987.

Hupe, Donald J., et al., "The Inhibition of Receptor–mediated and Voltage–dependent Calcium Entry by the Antiproliferative L–651, 582", *The Journal of Biological Chemistry*, vol. 266, No. 16, pp. 10136–10142, 1991.

Kohn, Elise, C., et al., "Autocrine Motility Factor Stimulates a Three–Fold Increase in Inositol Trisphosphate in Human Melanoma Cells", *Biochemical and Biophysical Research Communications*, vol. 166, No. 2, pp. 757–764, 1990.

Kohn, Elise, C., et al. "Autocrine Motility Factor Stimulates Phosphatidyl–Inositol Turnover in Human Melanoma Cells", *Proceedings of AACR*, vol. 29, 1988.

Kohn, Elise, C., et al., "L651582: A Novel Antiproliferate and Antimetastasis Agent", *Journal of the National Cancer Institute*, vol. 82, No. 1, 1990.

Kohn, Elise, C., et al., "L651582, A Novel Antiproliferate and Antimetastasis Agent Which Interferes with Guanine Nucleotide–Binding Protein Function", *Journal of the National Cancer Institute*, vol. 82, No. 1, 1990.

Merritt, Janet E., et al. "SK&F 96365, a novel inhibitor of receptor–mediated calcium entry", *Biochem. J.*, vol. 271, pp. 515–522, 1990.

Felder, Christian C., et al., "The Antiproliferative and Natimetastatic Compound L651582 Inhibits Muscarinic Acetylcholine Receptor–Stimulated Calcium Influx and Arachidonic Acid Release", *Journal of Pharmacology and Experimental Therapeutics*, vol. 257, No. 23, pp. 967–971, 1991.

Jones, David, T., et al., "Biochemical Characterization of Three Stimulatory GTP–binding Proteins", *The Journal of Biological Chemistry*, vol. 265, No. 5, pp. 2671–2676, 1990.

--- VEHICLE-STIMULATION OF INOSITOL PHOSPHATES
——— AMF-STIMULATION OF INOSITOL PHOSPHATES
○ - VEHICLE (DMSO) TREATED CELLS
● - CELLS PRETREATED WITH COMPOUND 1 AT 1 μg/ml

SIGNAL TRANSDUCTION INHIBITOR COMPOUNDS

This is a Divisional of application Ser. No. 08/270,181, filed Jul. 1, 1994, now U.S. Pat. No. 5,482,954 which is a Divisional of application Ser. No. 07/985,402 filed Dec. 4, 1992, now U.S. Pat. No. 5,359,078, which is a Continuation-In-Part of application Ser. No. 07/355,744 filed May 19, 1989, now U.S. Pat. No. 5,132,315, which is a Continuation-In-Part of Ser. No. 07/944,009, filed Sep. 11, 1992 (abandoned), which is a Continuation of Ser. No. 07/637,145, filed on Jan. 3, 1991 (abandoned), and a Continuation-In-Part of Ser. No. 07/894,891, filed on Jun. 8, 1992 (abandoned).

BACKGROUND OF THE INVENTION

The development of new and more effective chemotherapeutic agents for cancer treatment requires consideration of a variety of factors including cytotoxicity, tumor cell proliferation, invasion and metastasis. Conventional anticancer agents have typically been identified on the basis of their cytotoxicity alone, as the signaling pathways required for the maintenance and driving of the malignant process were not known. These pathways are now being elucidated in terms of signal transduction.

Signal transduction is the processing of chemical signals from the cellular environment through the cell membrane, and may occur through at least three distinct mechanisms: phosphorylation, activation of ion channels, and effector enzyme activation via guanine nucleotide binding protein intermediates.

Linkage of selected signal transduction pathways to malignant behavior has been demonstrated using molecular biologic techniques. Three different guanine nucleotide-binding protein-linked receptors have been transfected into normal recipient cells and upon specific ligand activation caused malignant behavior.

Tumor formation and ligand-specific focus formation was found when the serotonin 1c receptor was placed into NIH-3T3 cells and stimulated with a receptor specific ligand. Julius, et al., *Science*, 244:1057–1062 (1989). Serotonin stimulation of the transfected 5HT1c receptors resulted in mobilization of calcium, leading to a proposed link between receptor activation of the signal pathway and the biologic function of tumor formation.

A similar outcome was seen when an adrenergic alpha-1B receptor was put into NIH-3T3 and Rat-1 cells. Allen, et al., *Proc. Natl. Acad. Sci. USA* 88:11354–11358 (1991). In that experiment, catecholamine stimulation of the transfected receptor produced foci formation and increased cellular proliferation in culture as well as tumorigenic behavior in nude mice. Allen, et al. further demonstrated the functional coupling of the transfected receptor to production of total inositol phosphates which can secondarily cause internal release and influx of calcium, suggesting a link between these signal transduction pathways and the malignant response.

Lastly, transfection of the odd-numbered muscarinic receptors into NIH-3T3 cells has been shown to stimulate internal calcium release and uptake, arachidonic acid release, and generation of inositol phosphates. See, Bonner, et al., *Neuron*, 1:403–410 (1988), Gutkind, et al., *Proc. Natl. Acad. Sci. USA*, 88:4703–4703 (1991). Conklin, et al., *Proc. Natl. Acad. Sci. USA*, 85:8698–8702 (1988), and Felder, et al., *J. Pharmachol. Exp. Ther.*, 255:1140–1147 (1990). Additionally, ligand activation of the m1, m3, and m5 subtype muscarinic receptors resulted in tumorigenic foci formation in vitro.

Association of the products of the arachidonic acid cascade and generation or inhibition of malignancy has also been documented. Prostaglandins have been implicated in the initiation and promotion of malignancy. Honn, et al., *Prostaglandin* 21:833–864 (1981). In these experiments, phorbol esters stimulated the production of $PGE_2$ and $PGF_{2\alpha}$ which could be selectively inhibited by treatment with the cyclooxygenase inhibitor, indomethacin. Pharmacologic manipulation of prostaglandin synthesis in animal models led to the inhibition of cancer progression and was the impetus for human trials.

Pharmaceutical inhibition directed to specific pathways, such as arachidonic acid release or calcium influx, offers a new approach to cancer treatment and potentially to cancer prevention. Compound 1 was originally designed as a coccidiostat (U.S. Pat. No. 4,590,201) and later developed as a cancer treatment agent of particular use in the treatment of peritoneal carcinomatosis of ovarian cancer (U.S. Pat. No. 5,132,315, and Kohn, et al., *J. Natl. Cancer Inst.*, 82:54–60 (1990)). Recent studies have shown Compound 1 to be a novel inhibitor of selected signal transduction pathways including those which involve calcium influx, the release of arachidonic acid and the generation of inositol phosphates. See. Kohn, et al. *Cancer Res.*, 52:3208–3212 (1992) and Felder, et al., *J. Pharmacol. Exp. Ther.*, 257:967–971 (1991).

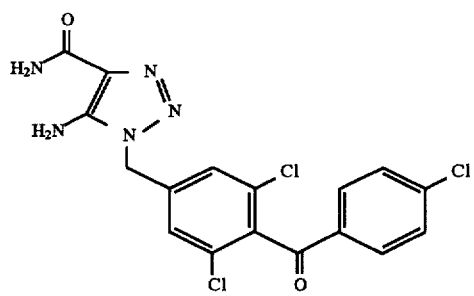

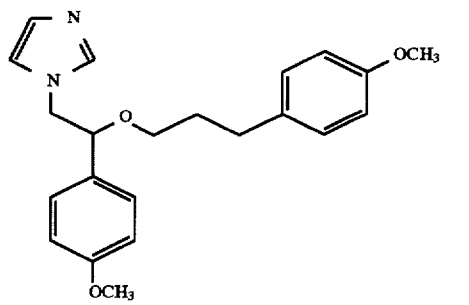

Compound 2 is another agent with selectivity for receptor-mediated calcium entry (RMCE). This compound inhibits RMCE in platelets, endothelial cells and neutrophils, and blocks voltage-gated L-type calcium channels in vascular smooth muscle cells under patch clamp. Merritt, et al., *Biochem. J.* 271:515–522 (1990). Similarly, compound 1 has been shown to inhibit L- and T-type voltage gated calcium channels. Hupe, et al., *J. Bio. Chem.*, 266:10136–10142 (1991). However, neither study evaluated the effect of their respective agents on malignant cells.

Signaling events are so primary in cellular function that any agent which interferes with signal-effector coupling should be uniformly toxic to normal cells and tissues as well as to malignant and metastatic tissues and cells. However, when nude mice received oral administration of compound 1. no toxicity to normal tissues including connective tissue, mucosal surfaces, and bone marrow was observed. See, Hupe, et al. *J. Cell. Physiol.*, 144:457–466 (1990) and Kohn, et al., *Cancer Research*, 52:3208–3212 (1992). This suggests that malignant cells have a higher state of dependence upon certain second messenger pathways, rendering them selectively sensitive to compound 1 and related agents.

SUMMARY OF THE INVENTION

One discovery underlying this invention is the concordance between particular cellular signaling mechanisms and cancer cell growth and metastasis. It has now been discovered that certain compounds inhibit the signal transduction required for the maintenance and driving of the malignant process. These compounds are also effective for the in vivo treatment of solid tumors and related disease states. This invention provides a method for the use of these compounds to inhibit the invasion and metastasis of malignant solid tumors in mammals. This invention further provides a method for using related compounds to treat diseases involving aberrant signal transduction pathways. Some of the compounds used in the methods of this invention are novel and constitute another aspect of the invention.

DESCRIPTION OF THE PREFERRED EMBODIMENTS

Figure 1:
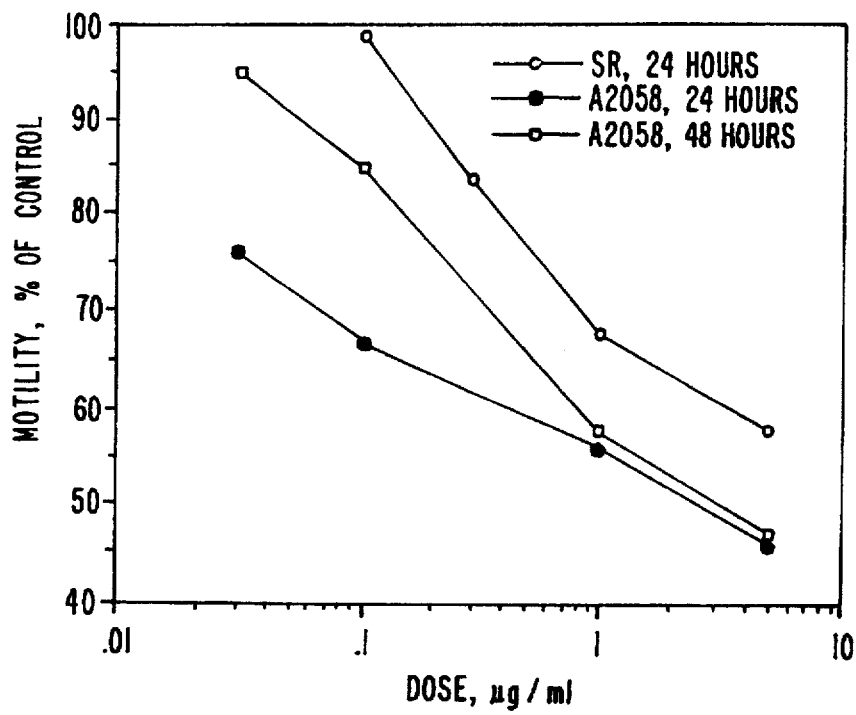
FIG. 1 shows the dose dependent inhibition by compound 1 of Table A below on autocrine motility factor (AMF)-stimulated chemotaxis. Compound 1 (0.03–10 µg/ml) inhibited AMF-stimulated tumor cell motility in a dose dependent manner. Slight inhibition of motility was seen with preincubation times of up to 8 hr; however, optimal inhibition required overnight treatment with 1 (5R, (O) 24 hr; A2058 (■) 24 hr, (□) 48 hr). Cell treatment with the combination of both 1 (1 µg/ml) and PT (0.1 µ/ml) did not result in greater inhibition of motility than either drug alone (data not shown).

The following abbreviations are used herein: CHO, Chinese Hamster ovary; G protein, guanine nucleotide binding protein; HEPES, 4-(2-hydroxyethyl)-1-piperazineethanesulfonic acid; CHOm5, Chinese Hamster ovary cell transfected with and stably expressing the gene for a muscarinic acetylcholine m5 receptor; PBS, phosphate-buffered saline; AMF, autotrine motility factor; PT, pertussis toxin; HPLC, high performance liquid chromatography; RMCE, receptor-mediated calcium entry; DMSO, dimethyl sulfoxide; PEG-400, poly(ethylene glycol)-400; DMEM, Dulbecco's modified Eagle's medium; IMEM, Incomplete modified Eagle's medium; BSA, bovine serum albumin; EDTA, ethylenediamine tetraacetic acid; fcs, fetal calf serum; PI, phosphatidyl inositol; qod, every other day.

As used herein, the term "alkyl" refers to a saturated hydrocarbon radical which may be straight-chain or branched-chain (for example, ethyl, isopropyl, t-amyl, or 2,5-dimethylhexyl). Preferred alkyl groups are those containing 1 to 6 carbon atoms. All numerical ranges in this specification and claims are intended to be inclusive of their upper and lower limits.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aromatic group" refers to a moiety which has multiple sites of unsaturation, and may be a single ring or multiple rings which are fused together or linked covalently. The aromatic rings may each contain heteroatoms, for example, phenyl, naphthyl, biphenyl, thienyl, pyridyl and quinoxalyl. The aromatic moieties may also be optionally substituted with halogen atoms, or other groups such as nitro, carboxyl, alkoxy and the like.

The term "alkoxyalkyl" refers to an alkoxy radical attached directly to an alkyl group.

The term "hydrophobic radical" refers to a group which lowers the water solubility of a molecule. Preferred hydrophobic radicals are groups containing at least 3 carbon atoms.

The term "solid tumor" refers to any malignancy exclusive of leukemia.

The term "substituted" refers to groups having additional moieties attached. Such moieties including halogen atoms, and groups such as nitro, carboxyl, alkoxy and the like.

The term "effective amount" refers to an amount sufficient to elicit the desired biological response. The desired response may be inhibition of tumor growth or signal transduction.

In one aspect, the present invention provides a method of inhibiting the invasion, metastasis and proliferation of malignant solid tumors in mammals using compounds of formula I or formula II.

$$Z-(CH_2)_p-Ar^1 \quad (I)$$

and

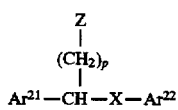

$$Ar^{21}-CH-X-Ar^{22} \quad (II)$$

The group $Ar^1$ is typically a hydrophobic radical. Examples of hydrophobic radicals for this group are phenyl, trioxaadamantyl, anthracenyl, anthraquinonyl, naphthyl, and phenanthryl. The radicals in this group may also be substituted. Additionally, $Ar^1$ may be $-Ar^2-X-Ar^3$.

$Ar^2$ and $Ar^3$ are typically aromatic groups and may be the same or different. Examples of aromatic groups are phenyl, substituted phenyl, naphthyl, and substituted naphthyl.

The symbol X represents a linking group and may be O, S, $SO_2$, CO, CHCN, straight chain alkyl, alkoxy, and alkoxyalkyl.

The group Z represents a nitrogen-containing heterocycle. Example of nitrogen-containing heterocycles for this group are imidazolyl, 1,2,3-triazolyl, 1,2,4-triazolyl, pyrazinyl, purinyl, pyrimidinyl, 1,2,3-triazolo-{4,5-d}-pyrimidinyl, and their substituted analogs.

The symbol p represents an integer of from 0 to 4.

In certain preferred embodiments, this method uses a compound of formula I in which $Ar^1$ is $-Ar^2-X-Ar^3$, $Ar^2$ and $Ar^3$ are both substituted phenyl, and Z is substituted or unsubstituted imidazolyl, 1,2,3-triazolyl, or 1,2,3-triazolo-{4,5-d}-pyrimidinyl.

In further preferred embodiments, this method uses a compound of formula I in which $Ar^1$ is $-Ar^2-X-Ar^3$, $Ar^2$ and $Ar^3$ are both substituted phenyl, and Z is substituted or unsubstituted imidazolyl or 1,2,3-triazolyl, X is CO, and p is 1.

In still further preferred embodiments, this method uses a compound of formula I in which $Ar^1$ is $-Ar^2-X-Ar^3$, $Ar^2$ is 2,6-dichlorophenyl, $Ar^3$ is 4-chlorophenyl, X is CO, Z is 5-amino-4-carboxamido-1,2,3-triazolyl, and p is 1.

In another group of preferred embodiments, the method uses compounds of formula II in which $Ar^2$ and $Ar^3$ are both substituted phenyl, and Z is substituted or unsubstituted imidizolyl, 1,2,3-triazolyl, or 1,2,3-triazolo-{4,5-d}-pyrimidinyl.

Further preferred embodiments within this group are methods which use compounds of formula II in which $Ar^2$ and $Ar^3$ are both substituted phenyl, X is CO, alkyl, alkoxy, or alkoxyalkyl. Z is substituted or unsubstituted imidizolyl or 1,2,3-triazolyl, and p is an integer of from 0 to 2.

In still further preferred embodiments within this group, the method uses compounds of formula II in which $Ar^2$ and $Ar^3$ are both substituted phenyl, X is alkoxy, Z is substituted or unsubstituted imidizolyl or 1,2,3-triazolyl, and p is 1.

In the most preferred embodiments within this group, the method uses either of two compounds of formula II. In the first compound, $Ar^2$ and $Ar^3$ are both 2,4-dichlorophenyl, X is $OCH_2$, Z is imidazolyl, and p is 1. In the second compound, $Ar^2$ and $Ar^3$ are both 4-methoxyphenyl, X is $OCH_2)_3$, Z is imidazolyl, and p is 1.

Another aspect of the present invention resides in a method for treating diseases in a subject in which those diseases involve aberrant signal transduction pathways. In this method, the treatment involves administering to the subject an effective amount of a compound of formula III.

$$Y-(CH_2)_p-Ar^{11}-X-Ar^{12} \quad (III)$$

The groups $Ar^{11}$ and $Ar^{12}$ are each aromatic moieties and may be the same or different. Examples of aromatic moieties for these groups are phenyl and naphthyl which may be further substituted.

The group X is a linking group which is O, S, $SO_2$, CO, CHCN, straight chain alkyl, alkoxy, or alkoxyalkyl.

The symbol Y represents a variety of structures. Some of these structures are represented by formula IV:

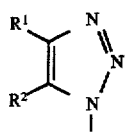

(IV)

in which $R^1$ is hydrogen, $-CONH_2$, $-CONHR^5$, $-CO_2H$, $-CO_2R^5$, or $-SO_2NH_2$; $R^2$ is hydrogen or $-NHCOC_6H_5$;

and $R^5$ is lower alkyl of from 1 to 6 carbon atoms. Preferred groups for $R^1$ are hydrogen, —$CONH_2$, —$CONHR^5$, and —$CO_2H$. Particularly preferred are —$CONH_2$ and —$CO_2H$.

Other structures for Y are radicals of formula V:

in which $R^3$ is hydrogen, —$CONH_2$, —$CONHR^5$, —CN, —$CONHNH_2$, —$C(=NH)NH_2$, —CONHOH, —$CO_2H$, —$CO_2R^5$, or —$SO_2NH_2$; $R^4$ is hydrogen, —$NH_2$, —$NHR^5$, —$N(R^5)_2$, —$NHCOR^5$, —NHCHO, —$NHC(=NH)R^5$, —NHCH(=NH), —$NHCONH_2$, or —$NHC(=NH)NH_2$; and $R^5$ is lower alkyl of from 1 to 6 carbon atoms. Preferred groups for $R^3$ are hydrogen, —$CONH_2$, and —$CONHR^5$. A particularly preferred group is —$CONH_2$. Preferred groups for $R^4$ are hydrogen, —$NH_2$, and —$NHR^5$.

Still other structures for Y are 1,2,4-triazolyl, pyrazinyl, purinyl, pyrimidinyl, 1,2,3-triazolo-{4,5-d}-pyrimidinyl, and their substituted analogs.

Most preferred among compounds of formula III is that structure in which $Ar^{11}$ is 2,6-dichlorophenyl, $Ar^{12}$ is 4-chlorophenyl, X is CO, p is 1, and Y is a radical of formula V in which $R^3$ is —$CONH_2$, and $R^4$ is —$NH_2$.

Still another aspect of the present invention resides in a method for treating diseases in a subject in which those diseases involve aberrant signal transduction pathways. In this method, treatment involved administering to the subject an effective amount of a compound having of formula VI:

in which $Ar^{21}$ and $Ar^{22}$ may be the same or different and are either phenyl, naphthyl, or their substituted analogs; X is O, S, $SO_2$, CO, CHCN, straight chain alkyl, alkoxy, and alkoxyalkyl; Z is imidazolyl, 1,2,3-triazolyl, 1,2,4-triazolyl, pyrazinyl, purinyl, pyrimidinyl, 1,2,3-triazolo-{4,5-d}-pyrimidinyl, or a substituted analog thereof; and p is an integer of from 0 to 4.

In certain preferred embodiments, $Ar^{21}$ and $Ar^{22}$ are both substituted phenyl; X is CO, alkyl, alkoxy, or alkoxyalkyl; Z is imidazolyl, 1,2,3-triazolyl, or their substituted analogs; and p is an integer of from 0 to 2.

In the most preferred embodiments within this group, the method uses either of two compounds of formula VI. For the first compound, $Ar^{21}$ and $Ar^{22}$ are both 2,4-dichlorophenyl, X is $OCH_2$, Z is imidazolyl and p is 1. For the second compound, $Ar^{21}$ and $Ar^{22}$ are both 4-methoxyphenyl, X is $O(CH_2)_3$, Z is imidazolyl, and p is 1.

A still further aspect of the present invention resides in a method for treating diseases involving aberrant signal transduction by administering to a subject, an effective amount of a compound of formula VII:

in which $Ar^{31}$ is phenyl, trioxaadamantyl, anthracenyl, anthraquinonyl, naphthyl, phenanthryl, or a substituted analog thereof; Z is imidazolyl, 1,2,3-triazolyl, 1,2,4-triazolyl, pyrazinyl, purinyl, pyrimidinyl, 1,2,3-triazolo-{4,5-d}-pyrimidinyl, or a substituted analog thereof; and p is an integer of from 0 to 4.

A still further aspect of the present invention resides in novel compounds which are useful for the treatment of diseases involving aberrant signal transduction. In one embodiment these novel compounds are represented by formula III.

The groups $Ar^{11}$ and $Ar^{12}$ are each aromatic moieties and may be the same or different. Examples of aromatic moieties for these groups are phenyl and naphthyl which may be further substituted.

The group X is a linking group which is O, S, $SO_2$, CO, CHCN, straight chain alkyl, alkoxy, or alkoxyalkyl.

The symbol Y represents a variety of structures. Some of these structures are represented by formula IV:

in which $R^1$ is hydrogen, —$CONH_2$, —$CONHR^5$, —$CO_2H$, —$CO_2R^5$, or —$SO_2NH_2$; $R^2$ is hydrogen or —$NHCOC_6H_5$; and $R^5$ is lower alkyl of from 1 to 6 carbon atoms. Preferred groups for $R^1$ are hydrogen, —$CONH_2$, —$CONHR^5$, and —$CO_2H$. Particularly preferred are —$CONH_2$ and —$CO_2H$.

Other structures for Y are radicals of formula V:

in which $R^3$ is hydrogen, —$CONH_2$, —$CONHR^5$, —CN, —$CONHNH_2$, —$C(=NH)NH_2$, —CONHOH, —$CO_2H$, —$CO_2R^5$, or —$SO_2NH_2$; $R^4$ is hydrogen, —$NH_2$, —$NHR^5$, —$N(R^5)_2$, —$NHCOR^5$, —NHCHO, —$NHC(=NH)R^5$, —NHCH(=NH), —$NHCONH_2$, or —$NHC(=NH)NH_2$; and $R^5$ is lower alkyl of from 1 to 6 carbon atoms. Preferred groups for $R^3$ are hydrogen, —$CONH_2$, and —$CONHR^5$. A particularly preferred group is —$CONH_2$. Preferred groups for $R^4$ are hydrogen, —$NH_2$, and —$NHR^5$.

Still other structures for Y are 1,2,4-triazolyl, pyrazinyl, purinyl, pyrimidinyl, 1,2,3-triazolo-{4,5-d}-pyrimidinyl, and their substituted analogs.

Most preferred among compounds of formula III is that structure in which $Ar^{11}$ is 2,6-dichlorophenyl, $Ar^{12}$ is 4-chlorophenyl, X is CO, p is 1, and Y is a radical of formula V in which $R^3$ is —$CONH_2$, and $R^4$ is —$NH_2$.

In another group of preferred embodiments, the novel compounds that are useful for the treatment of diseases involving aberrant signal transduction may be represented by formula VII.

in which $Ar^{31}$ is phenyl, trioxaadamantyl, anthracenyl, anthraquinonyl, naphthyl, phenanthryl, or a substituted analog thereof; Z is imidazolyl, 1,2,3-triazolyl, 1,2,4-triazolyl, pyrazinyl, purinyl, pyrimidinyl, 1,2,3-triazolo-{4,5-d}-pyrimidinyl, or a substituted analog thereof; and p is an integer of from 0 to 4. Particularly preferred are compounds of formula VII in which p is 1, $Ar^{31}$ is phenyl or substituted phenyl, and Z is imidazolyl or 1,2,3-triazolyl, and their substituted analogs.

The compounds used in the present invention are either commercially available or may be prepared using conventional synthetic techniques. General synthetic routes to the novel compounds tested are provided below. Particular conditions are known to those of skill in the art. The tables below provide examples of the compounds evaluated in developing the present invention.

TABLE A

| Compound Number | A | B | C |
|---|---|---|---|
| 1 | N | carboxamido | amino |
| 3 | N | carboxamido | formamido |
| 4 | N | carboxamido | acetamido |
| 5 | N | carboxamido | benzamido |
| 6 | N | carboxyl | amino |
| 7 | CH | — | — |
| 8* | N | carboxamido | amino |

*all Cl are replaced by H

TABLE B

| Compound Number | A | B | C |
|---|---|---|---|
| 9 | CH | carboxamido | amino |
| 10 | N | carboxyl | carboxyl |

TABLE C

| Compound Number | D | E |
|---|---|---|
| 11 | F | H |
| 12 | Cl | H |
| 13 | Br | H |
| 14 | I | H |
| 15 | Cl | Cl |
| 16 | F | F |

TABLE D

| Compound Number | L | D | E | G | J | K |
|---|---|---|---|---|---|---|
| 17 | H | H | H | H | H | H |
| 18 | F | H | H | H | H | H |
| 19 | Cl | H | H | H | H | H |
| 20 | Br | H | H | H | H | H |
| 21 | H | H | Cl | H | H | H |
| 22 | Cl | H | H | Cl | H | H |
| 23 | H | H | Cl | F | H | H |
| 24 | H | H | F | F | H | H |
| 25 | H | H | OH | H | H | OH |
| 26 | CH$_2$OH | Cl | Cl | Cl | H | H |

Compound 1 can be prepared by the method described in U.S. Pat. No. 4,590,201.

Compound 2 can be prepared by the method described in Merritt, et al., *Biochem. J.*, 271:515–522 (1990).

Compounds 3–5 are prepared by treating compound 1 with the appropriate anhydride (formic acetic anhydride, acetic anhydride, or benzoic anhydride).

Compound 6 can be prepared by treating compound 1 with sufficient acid to hydrolyze the carboxamide to a carboxylic acid.

Compound 7 can be prepared by the conversion of compound 26 to the corresponding benzyl halide derivative, followed by the reaction of that halide with imidazole in the presence of base.

Compound 8 can be synthesized beginning with 4-methylbenzophenone. Treatment of 4-methylbenzophenone with N-bromosuccinimide provides 4-bromomethylbenzophenone which is converted to its corresponding azide using sodium azide in ethanol. Treatment of the resultant azide with the anion of 2-cyanoacetamide provides compound 8.

Compounds 11–13 may be synthesized beginning with their corresponding 3-halo-benzylbromides. Conversion of the bromide to an azide can be accomplished using sodium azide in ethanol. The products are then obtained by treating the resultant 3-halobenzyl azides with the anion of 2-cyanoacetamide.

Compound 14 can be obtained beginning with 3-iodobenzylamine. This amine can be converted to its corresponding azide by forming a 2,4,6-triphenylpyrylium derivative and subsequently displacing the pyrylium species using sodium azide. The azide may be treated as above to provide compound 14.

Compounds 15 and 16 can be prepared from 3,5-dichlorobenzamide and 3,5-difluorobenzamide, respectively. In this instance, the benzamide is reduced to 3,5-dihalobenzylamine and the steps used for compound 14 are employed.

Compound 26, an intermediate in the preparation of compound 1, can be prepared in several steps beginning with 3,5-dichlorobenzyl alcohol. The alcohol is protected as a t-butyldimethylsilyl ether, then treated with n-butyllithium followed by 4-chlorobenzoyl chloride to produce 4-(t-butyldimethylsilyloxymethyl-2,4',6-trichlorobenzophenone. Removal of the silyl protecting group provides compound 26.

The compounds used in the present inventive method may be administered in any suitable manner, preferably with pharmaceutically acceptable carders. One skilled in the art will appreciate that suitable methods of administering such compounds in the context of the present invention to an animal are available, and, although more than one route can be used to administer a particular compound, a particular route can provide a more immediate and more effective reaction than another route. Pharmaceutically acceptable carriers are also well-known to those who are skilled in the art. The choice of carrier will be determined in part by the particular compound, as well as by the particular method used to administer the composition. Accordingly, there is a wide variety of suitable formulations of the pharmaceutical composition of the present invention.

Formulations suitable for oral administration can consist of (a) liquid solutions, such as an effective mount of the compound dissolved in diluents, such as water, saline or PEG 400; (b) capsules, sachets or tablets, each containing a predetermined amount of the active ingredient, as solids, granules or gelatin: (c) suspensions in an appropriate liquid: and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium sterate, stearic acid, and other excipients, colorants, fillers, binders, diluents, buffering agents, mositening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such as carriers as are known in the art.

The active ingredient, alone or in combination with other suitable components, can be made into aerosol formulations to be administered via inhalation. These aerosol formulations can be placed into pressurized acceptable propellants, such as dichlorodifluoromethane, propane, nitrogen, and the like.

Suitable formulations for rectal administration include, for example, suppositories, which consist of the active ingredient with a suppository base. Suitable suppository bases include natural or synthetic triglycerides or paraffin hydrocarbons. In addition, it is also possible to use gelatin rectal capsules which consist of a combination of the active ingredient with a base, such as, for example, liquid triglyercides, polyethylene glycols, and paraffin hydrocarbons.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compound employed and the condition of the animal, as well as the body weight or surface area of the animal to be treated. The size of the dose also will be determined by the existence, nature, and extent of any adverse side-effects that might accompany the administration of a particular compound in a particular animal. In determining the effective amount of the active ingredient to be administered in the treatment or prophylaxis of cancer treatment, the physician needs to evaluate circulating plasma levels, toxicities, and tumor growth inhibition, and evidence of cancer progression.

In the practice of this invention, the compounds can be administered, for example, by intravenous infusion, orally, topically, intraperitoneally, intravesically or intrathecally for treatment of lymphomas, leukemias, and all solid tumors. The compounds could be applied in a suitable vehicle for the local and topical treatment of cancer. Tumors such as basal cell carcinoma and Kaposi's sarcoma could be treated by topical administration of the agents taught herein. Prevention of tumor recurrence by administration of the composition in a manner intended to reach the particular site where such cells are proliferating would be most advantageous. For example, intraperitoneal administration would be a means of treating tumors known to cause peritoneal carcinomatosis. Intravesical treatment of transitional cell carcinoma and topical treatment of mycosis fungoides are further examples of site-directed treatment. Systemic administration may be accomplished by continuous infusion, bolus parenteral treatment, or release from an implanted slow release depot. It is obvious that this method can supplement treatment of cancer by any conventional therapy including cytotoxic agents and biologic response modifiers. The method disclosed may be used in any malignancy as a means of treatment to prevent the transition from in situ to invasive carcinoma or invasive to metastatic carcinoma.

For oral administration, compounds of the present inventive method can be administered at the rate up to 3000 mg/m$^2$ body surface area, which approximates 6 grams/day in the average patient. This can be accomplished via single or divided doses. For intravenous administration, such compounds can be administered at the rate of up to about 2500 mg/m$^2$/d. For intravesicle administration, such compounds can be administered at the rate of up to about 2500 mg/m$^2$/d. For topical administration, the rate can be up to about 2500 mg/m$^2$/d. The dose for inhalation/aerosol administration can be up to about 2500 mg/m$^2$/d. Direct intraperitoneal administration can be performed using up to about 3000 mg/m$^2$/d. The dose for reservoir administration to the brain or spinal fluid can be up to about 2000 mg/m$^2$/d. For slow release intraperitoneal or subcutaneous administration, the dose can be up to about 10 g/day in a bolus. For intrathecal administration, the dose can be up to about 2000 mg/m$^2$/d.

The methods taught herein are not restricted to use in treatment of malignancies. Disease conditions such as endometriosis, psoriasis, and eczema which result from localized spread of diseased cells may also be advantageously treated. Additionally, disease states which rely on aberrant signal transduction/proliferation may also be treated. Diseases of potentially aberrant signal transduction/ proliferation may include the collagen vasculitides (i.e., systemic lupus erthythematosis and rheumatoid arthritis), neurologic diseases (i.e., dementia and nerve conduction diseases), diseases of transport (i.e., cystic fibrosis), toxic effects of agents (i.e., cisplatin-related neuropathy), and cellular dysfunction (i.e., myelodysfunction syndromes).

The following examples illustrate the in vitro and in vivo assays and results used to evaluate the efficacy of the compounds of this invention. The examples further establish the concordance between signal transduction and tumor invasion and metastasis.

EXAMPLES

Materials

Compound 1 (Table A above) was supplied as a powder by the Developmental Therapeutics Program of the National Cancer Institute. A 20 mg/mL stock solution was made in DMSO or PEG-400, and aliquots were stored at −70° C. For use, a 10 µg/mL solution was prepared daily in media (DMEM), and serial dilutions were made as needed. Compound 2 was supplied by SmithKline Beecham Pharmaceuticals, The Frythe, Welwyn, Herts, UK. Compounds 9, 10, and 16–24 were purchased from Aldrich Chemical Co. (Milwaukee, Wis., USA).

Radiolabelled reagents were purchased from commercial sources: [$^3$H]inositol (specific activity 105 mCi/mg) and [$^3$H]thymidine (specific activity 102 mCi/mg), were purchased from Amersham (Arlington Heights, Ill., USA) and [$^3$H]arachidonic acid was purchased from DuPont/New England Nuclear (Baston, Mass., USA). Fura-2 was purchased from Molecular Probes (Portland, Oreg., USA). Dowex anion exchange resin 1-X8, formate form, was obtained from Bio-Rad (Rockville Center, N.Y., USA). The motility chamber and nucleopore filters (8µ, polyvinylpyrrolidone-free) were obtained from Neuro Probe, Inc. (Cabin John, Md., USA). Type IV collagen and laminin was obtained from Collaborative Research (Bedford, Me., USA). Phenol red-free IMEM with low inositol (2.7 nM) was obtained from the NIH media unit. Other reagents were either reagent grade or HPLC grade from commercial sources (Sigma Chemical Co., St. Louis, Miss., USA and Aldrich, Milwaukee, Wis., USA).

The cell lines were obtained from the American Type Culture Collection. (Rockville, Md., USA) with the exception of those listed below:

MCF-7 mdr+ human breast cancer line, resistant to adriamycin, was donated by Dr. Ken Cowan (Division of Cancer Treatment, National Cancer Institute, Bethesda, Md., USA);

A2058 was derived from a brain metastasis of a patient with melanoma (see, Todaro, et al., *Proc. Natl. Acad. Sci. USA*, 77:5258–5262 (1980));

5R, rat embryo fibroblast transfected with the activated Ha-ras gene was genetically engineered. See, Pozzatti, et al., *Science*, 232:223–227 (1986).

CHOm5, Chinese hamster ovary cells transfected with the m5 muscarinic receptor were provided by Dr. Chrisitan C. Felder (Laboratory of Cell Biology, National Institute of Mental Health, Bethesda, Md., USA).

Autocrine Motility Factor was prepared from A2058 cells as described in U.S. Pat. No. 5,132,315.

Methods and Results

A. In Vitro tests

Example 1

Cell Motility

This example describes the effect of compound 1 on tumor cell motility. This property of motility, or locomotion, is an integral part of the metastatic process. The effect of compound 1 on tumor cell motility was evaluated by incubating the tumor cells with the compound and subsequently monitoring cell migration relative to a vehicle treated control.

The cell motility assay has been described. See, Stracke et al., *Biochem. Biophys. Res. Comm.*, 146:339–345 (1987). Cells from the A2058 human melanoma line which was maintained in subconfluent culture were harvested with trypsin-EDTA, and were allowed to recover for 1 hr at room temperature. Cells from the 5R H-ras transformed (diploid) rat embryo fibroblast line were harvested with 2 mM EDTA in PBS without divalent cations. Cells were resuspended in serum-free media containing 0.1% BSA. This DMEM/0.1% BSA was used as the control for all subsequent assays. The assays were performed in triplicate using a 48-well chemotaxis chamber with 8µ Nucleopore, type IV collagen-coated filters. The chambers were incubated at 37° C. for 4 hr, stained and placed onto glass slides with the original cell side up so that the cell pellet could be wiped from the surface. Cells that had migrated through the pores were trapped between glass and membrane and could be quantitated by laser densitometry.

Compound 1 was preincubated with the cells for various periods of time, added at the start of the assay, or added later. Additionally, compound 1 remained present during the motility assay. The cells were assayed for their motile response to AMF. AMF stimulates random and directed locomotion of 5R ras-transfected rat embryo fibroblasts and A2058 human melanoma cells. This motility is markedly inhibited by cell treatment with pertussis toxin (PT), a known modulator of G protein function (PT, 0.5 µg/ml for 2 hr). Cell viability determined by trypan blue exclusion averaged greater than 96%. Cells exposed to various concentrations of compound 1 were tested for their response to AMF vs. control. Percent stimulated motility (in densitometer units) is defined as:

$$(\text{AMF stimulated-control})_{compound\ 1} / (\text{AMF stimulated-control})_{untreated}$$

The results observed on preincubation of either the A2058 or 5R cells with compound 1 are shown in FIG. 1. Overnight preincubation yielded reproducible dose-dependent decreases in stimulated motility of up to 55%. Increasing the time of exposure to 48 hr did not result in further inhibition of AMF-stimulated motility. The motile responses to AMF stimulation of two human breast cancer cell lines SKBR and MDA-231 were also inhibited after overnight exposure to compound 1 (data not shown).

Reversibility of cell motility which had been inhibited by compound 1 was determined by removing the compound from the incubation media. Thus, A2058 melanoma cells were cultured for 24 hr in standard media (DMEM/10% FCS), washed twice with saline, and cultured with DMEM/10% FCS with (+) or without (−) compound 1 for 24 hr. Cells were then washed and the treatments were reversed. The resulting cells are classified as "treated" (−/+, run as a control to test cell response following the incubation and washing steps), "washout" (+/−, run to evaluate reversibility), and "control". Control cells were washed and fed with standard media alone at each change point. Table E provides the results expressed as a percent of control cell motility at two concentrations of compound 1. As the results indicate, the effect of compound 1 could be reversed by removal of the compound from the culture medium.

TABLE E

Evaluation of the reversibility of compound 1 inhibition of tumor cell motility

|  | 5 µg/mL (+/−) | 5 µg/mL (−/+) | 1 µg/mL (+/−) | 1 µg/mL (−/+) |
| --- | --- | --- | --- | --- |
| Motility (% of control) | 94 | 27 | 97 | 59 |

TABLE F

Evaluation of the reversibility of compound 1 inhibition of tumor cell adhesion

|  | 5 µg/mL (+/−) | 5 µg/mL (−/+) | 1 µg/mL (+/−) | 1 µg/mL (−/+) |
| --- | --- | --- | --- | --- |
| Adhesion (% of control) | 96 | 37 | 106 | 33 |

The effect of compound 1 on tumor cell motility in response to laminin was also determined. Laminin is an important component of basement membrane and stimulates migration of tumor cells in vitro. Laminin-stimulated cell migration was carried out as described above, except that laminin (100 µg/mL) was used in place of AMF, and the number of migrated cells per high power field (400×) was determined by eye-counting. OVCAR3 cells were preincubated with or without compound 1 (1 µg/mL) for 18 hr prior to the motility assay.

Figure 2:
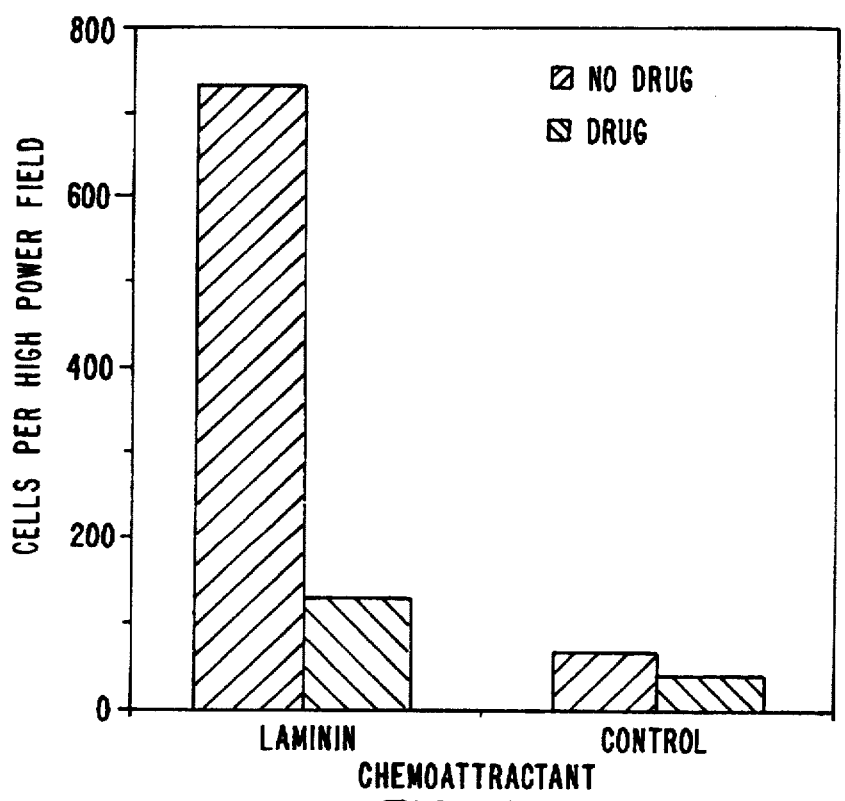
FIG. 2 shows the inhibition of laminin-stimulated OVCAR3 motility by 1. OVCAR3 is a tumor cell line derived from the malignant ascites of a patient with progressive ovarian cancer.

The results, shown in FIG. 2, demonstrate that compound 1 inhibited both spontaneous motility in response to control attractant (media with 0.1% BSA) and motility which was stimulated by laminin. Compound 1 also inhibited motility of A2058 and OVCAR3 cells due to type IV collagen stimulation (data not shown).

Example 2

Cell Adhesion

This example illustrates the effect of compound 1 on tumor cell adhesion. Two cell lines were examined to determine this effect. Like motility, the adherent properties of tumor cells are a key component of their metastatic spread.

An adhesion assay was developed using tissue culture plastic petri dishes as the substrate. Aliquots of cells treated similarly to those in the cell motility assay were plated in triplicate onto the dishes and incubated for 90 min at 37° C. Cells which were either poorly adherent or nonadherent were gently washed off with PBS. The remaining cells were stained with Diff Quik™ (from Baxter Scientific Products, McCaw Park, Ill., USA). Adherence was quantitated using laser densitometry and values were calculated as a percentage of the control adherence.

Figure 3:
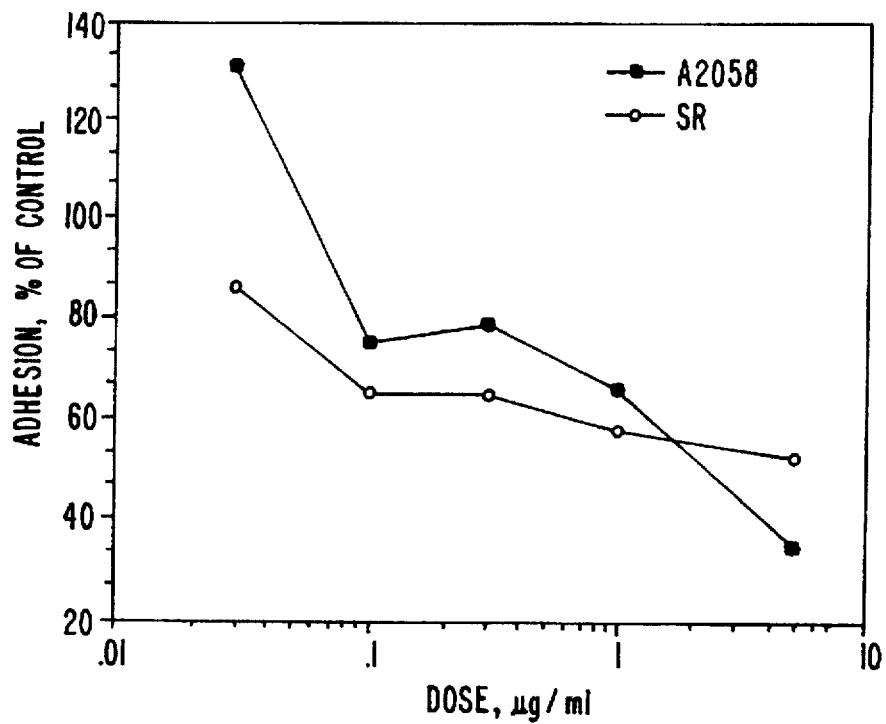
FIG. 3 shows the dose dependent inhibition by 1 on tumor cell adhesion to tissue culture plastic. As seen with motility, inhibition of adhesion was maximal after overnight exposure to the drug for 5R (O) and A2058 (■). Compound 1 also decreased cell adhesion to the matrix components laminin and fibronectin (data not shown). Cell spreading was not markedly decreased.

When either A2058 or 5R cells were treated with compound 1, dose-dependent inhibition of cell adhesion was observed. Cells were preincubated with compound 1 (0.03–10 µg/mL) for periods of 2 to 48 hr prior to the adhesion assay. In addition, compound 1 remained present during the assay. Preincubation periods of 2 to 4 hr resulted in only a small dose-dependent inhibition of adhesion. Maximal inhibition of adhesion was observed following overnight exposure of the cells to compound 1. These results are shown in FIG. 3. Compound 1 also decreased cell adhesion to the matrix components, laminin and fibronection (data not shown). However, cell spreading was not markedly decreased.

As with cell motility, the effect of compound 1 on cell adhesion is reversible. A2058 and 5R cells were treated as above for testing the reversibility of cell motility. The resulting "treated" cells (−/+), "washout" cells (+/−), and "control" cells were then subjected to the adhesion assay. The results for the two concentrations tested are shown in Table F.

Example 3

Cell Growth—Proliferation and Colony Formation

This example illustrates the effect of selected compounds on tumor cell growth, including both cell proliferation and colony formation. The effect of compound 1 on the growth of various tumor cell lines is shown. Additionally, selected compounds were evaluated for their effect on proliferation and colony formation of the A2058 cell line.

Proliferation: Two independent methods were used to determine the effect of various compounds on cellular proliferation. The first method utilized [$^3$H]thymidine labelling and was performed using A2058, 5R, OVCAR3, and MDA-231 cells. Because the potential effect of compound 1 on thymidine metabolism was unknown, a clonogenic assay was also used. This assay utilized crystal violet nuclear staining.

Figure 4:
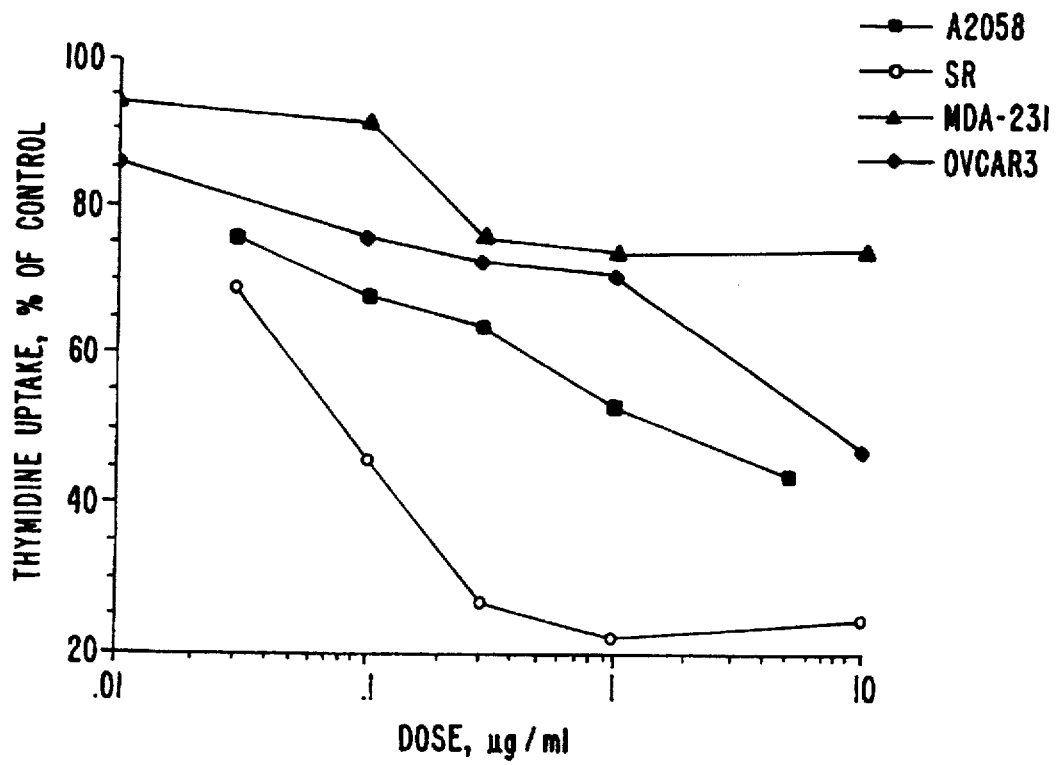
FIG. 4 shows the dose dependent inhibition of [$^3$H] thymidine incorporation by 1. Cells: A2058 (■), 5R (O), MDA-231 human breast cancer (▲), and OVCAR3 human ovarian cancer (♦). Data are expressed as percent of untreated control cell incorporation of labelled thymidine.

For the thymidine incorporation assay, an initial aliquot of 15,000 cells was plated in 96 well plates. The cells were grown to subconfluence, serum-starved, then fed with serum-containing media to which incremental doses of compound 1 (0–10 µg/mL) were added. After 24 hr, the cells were pulsed with [$^3$H]thymidine (0.5 µCi/well) for 2 hr. Trichloroacetic acid was added to precipitate unincorporated [$^3$H]thymidine. After removal, ice cold ethanol/diethyl ether was added to precipitate cellular nucleic acids. The residue was solubilized with 0.2M NaOH and [$^3$H]thymidine incorporation was determined by liquid scintillation counting. Inhibition of thymidine uptake was calculated as a percent of untreated control cell incorporation of labelled thymidine. The results are shown in FIG. 4. As FIG. 4 indicates, de novo DNA synthesis was inhibited in all of the tumor cell lines. Maximal inhibition (80%) was found with the 5R cells.

Figure 5:
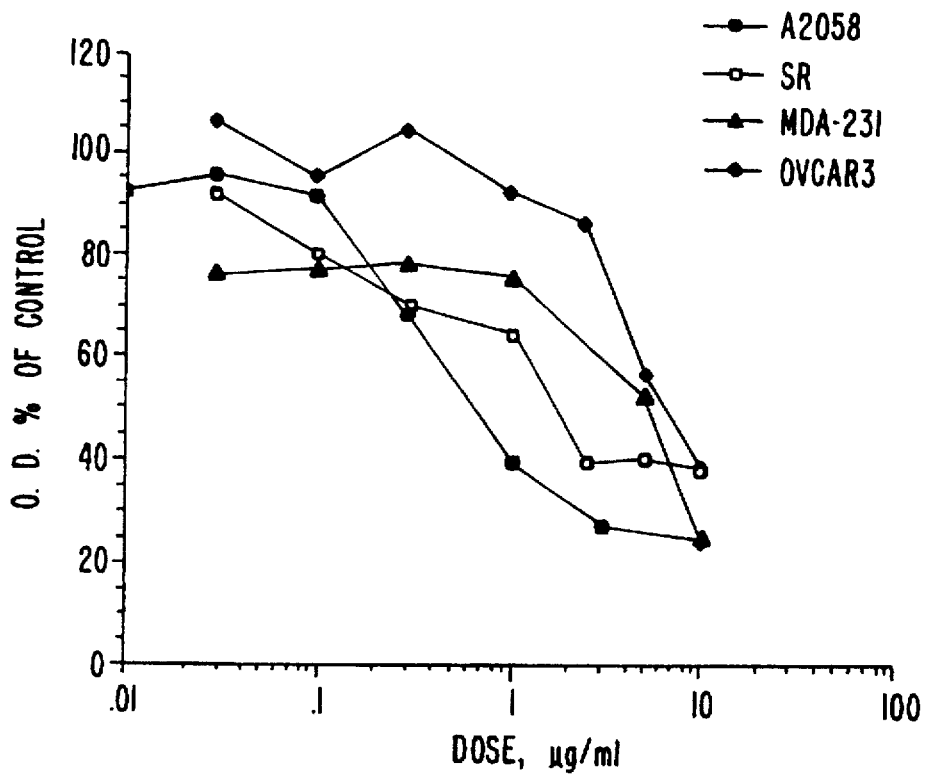
FIG. 5 shows the dose dependent inhibition of tumor cell proliferation by 1. Cells: A2058 (■), 5R (O), MDA-231 (▲), and OVCAR3 (♦).

For the clonogenic assay, aliquots of 50,000 cells per well (24 well plates) were grown under standard tissue culture conditions in the presence of increasing doses of test compound (0–10 µg/mL) or vehicle control. After 96 hr, the cells were gently washed with PBS, fixed, and stained with 0.5% crystal violet nuclear stain in 20% methanol. Excess stain was removed with tap water and bound stain was eluted with an equal volume solution of 0.1N sodium citrate (pH 4.2) and absolute ethanol. Optical density (O.D.) of eluted crystal violet stain was determined at 540 nm. The results of dose-dependent inhibition of tumor cell proliferation by compound 1 are shown in FIG. 5, in which the data are expressed as percent of untreated control cell proliferation for each cell type. The degree of inhibition varied with the cell type and was maximal (76%) for the A2058 cell line.

Additionally, compound 1 inhibited proliferation of a variety of human tumor and rodent cell lines in culture, including lines carrying activating oncogenes such as the T-24 human bladder cancer which has activated H-ras. In one study, the cells were continuously exposed to 20 µM compound 1, and growth inhibition was measured. In a second study, cell lines which only grow in suspension were plated in 24 well plates (50,000 cells/well) and were incubated with increasing concentrations of compound 1. After 72 hr in culture, the cells were harvested, centrifuged, resuspended in a small volume. The number of remaining cells and their viability was determined using a hemocytometer. Those cell lines which showed >80% inhibition at concentrations of 5–10 µg/mL are noted in Table G.

TABLE G

The Effect of Compound 1 on Growth of Human and Non-Human Tumor Cell Lines

| TUMOR CELL LINE | % GROWTH INHIBITION |
|---|---|
| HUMAN | >80% @ 5–10 µg/mL |
| A2058 melanoma | X |
| MDA-231 breast | X |
| CEM lymphoma | X |
| HuT-78 mycosis fungoides | X |
| HuT-102 mycosis fungoides | X |
| PC3 prostate | X |
| HT-29 colon | X |
| Panc-1 pancreas | X |
| OVCAR3 ovarian | X |
| RPMI-8226 plasmacytoma | X |
| MCF-7 breast | X |
| MCF-7 adriamycin-resistant breast (mdr$^+$) | X |
| T24 (EJ) bladder | X |
| H4 neuroglioma brain | X |
| A172 glioblastoma brain | X |
| NON-HUMAN | |
| mAChR-transfected CHO | X |
| B16F10 murine melanoma | X |
| 5R ras-transfected rat embryo fibroblasts | X |
| L1210 murine leukemia | X |
| PMT rat fibrosarcoma | X |
| A-raf transfected 10T1/2 | X |
| fms-1 transfected 10T1/2 | X |
| mos-2 transfected 10T1/2 | X |

Figure 20A:
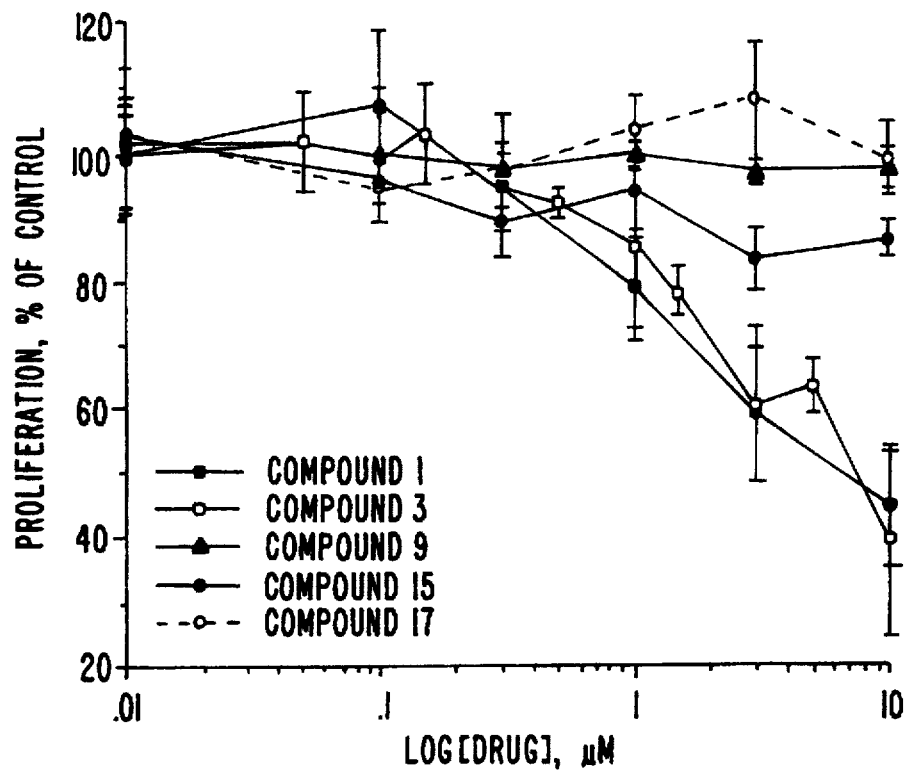
FIG. 20 shows the dose response results and $IC_{50}$ concentrations for inhibition of proliferation. The compounds were tested in the monolayer growth assays described in the Examples. A. Dose dependent inhibition of proliferation by 1 and 3, but not by compounds 8–26 (represented in the Figure by compounds 9, 15, and 17). B. $IC_{50}$ concentrations for inhibition of proliferation. Compounds not shown, but listed in Table H, had projected $IC_{50}$ values greater than 400 µM.
Figure 20B:
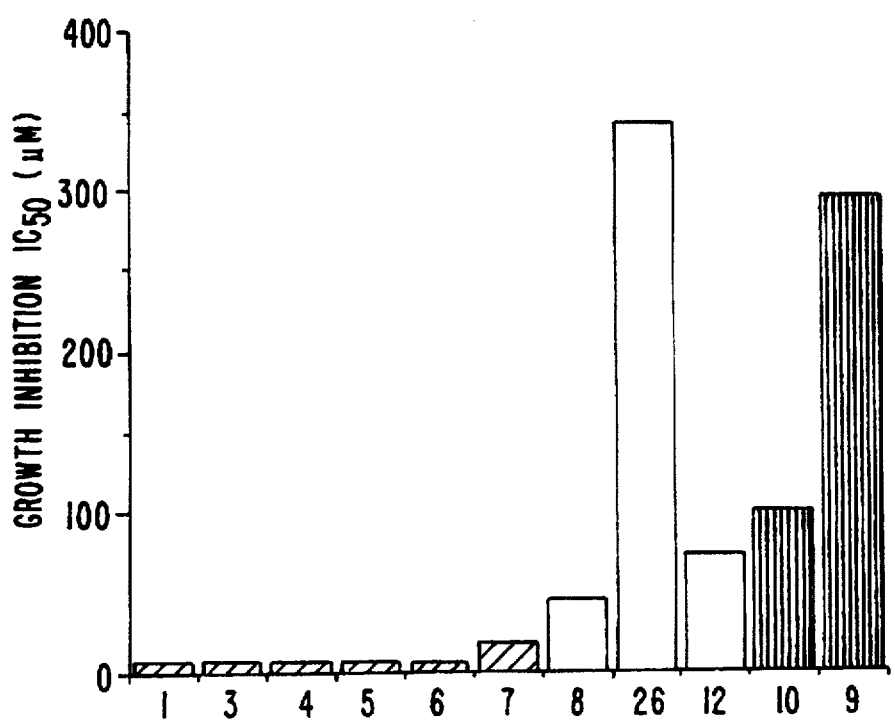

A2058 human melanoma cells were used to test the effect of compounds 1 and 3–25 on cellular proliferation. The cells were cultured in the presence of the test compounds (10 µM) for 96 hr, fixed and stained with crystal violet as described above. Growth inhibition was determined as a percent of control growth (using either DMSO or PEG-400 as the vehicle) for each compound. Each experiment was run a minimum of three times and the average of the results for each compound is provided in Table H and in FIGS. 20A and 20B.

Figure 6:
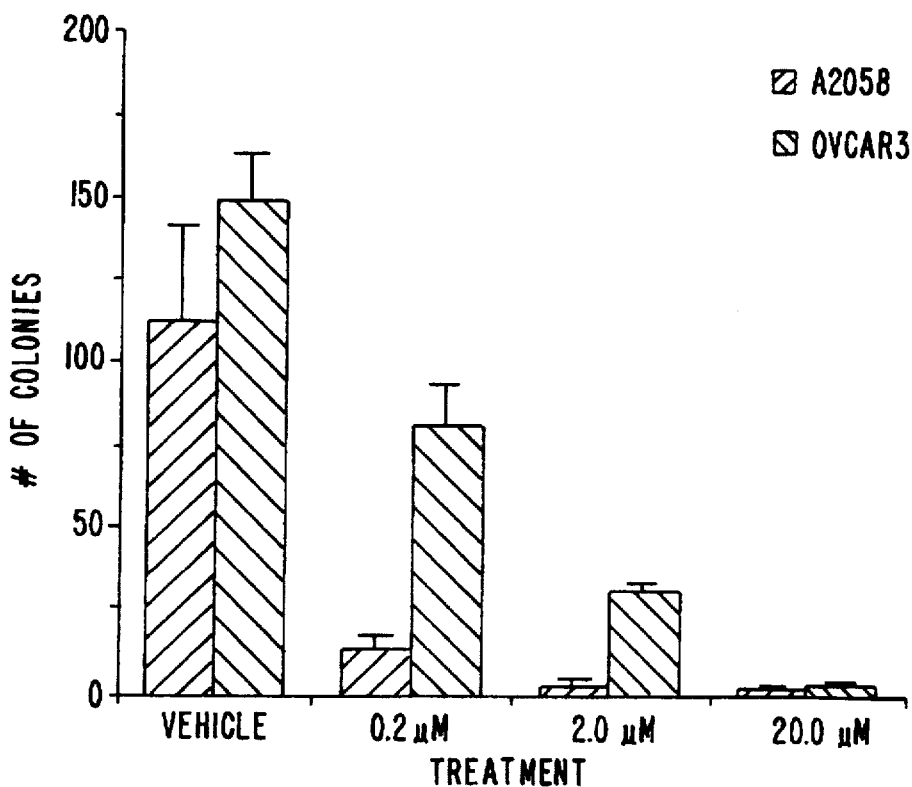
FIG. 6 shows the evaluation of 1 effect upon soft agar colonization of A2058 human melanoma and OVCAR3 human ovarian cancer cell lines. Quantitation of colony formation.

Colony formation: Compound 1 was evaluated at three concentrations for inhibition of colony formation in both the A2058 and OVCAR3 cell lines. Colony number was determined in triplicate and compared to the vehicle control run on each 24 well plate to provide a percent. The results are shown in FIG. 6. Colonies greater than 60 cells were counted at 100× under phase contrast. As FIG. 6 indicates significant inhibitory effects were seen when the A2058 cells were exposed to compound 1 at concentrations as low as 0.2 µM. The OVCAR3 line showed >70% inhibition at 2.0 µM 1. In a second study, selected compounds were evaluated for their effect on density-independent growth of the A2058 cell line in soft agar. Percent inhibition was determined over triplicate experiments involving three log molar concentrations of the test compound. The results are provided in Table H.

Table H

The Effect of Selected Compounds on Proliferation and Colony Formation of A2058 Cells

| TEST COMPOUND | GROWTH (% OF CONTROL) | COLONY FORMATION (% OF CONTROL) |
|---|---|---|
| 1 | 36.4 ± 6 | 11.1 ± 5 |
| 3 | 31.5 ± 7 | 10.2 ± 0.5 |
| 4 | 53.7 ± 15 | 10.3 ± 0.4 |
| 5 | 39.0 ± 2 | 9.97 ± 1 |
| 6 | 45.3 ± 11 | 9.00 ± 1 |
| 7 | 66.5 ± 9 | |
| 8 | 92.7 ± 9 | 93.4 ± 3 |
| 9 | 97.0 ± 3 | |
| 10 | 92.2 ± 4 | 100 ± 3 |
| 11 | 89.0 ± 3 | |
| 12 | 85.0 ± 2 | |
| 13 | 85.5 ± 13 | |
| 14 | 89.0 ± 6 | |
| 16 | 111 ± 8 | |
| 17 | 98.5 ± 5 | 95.9 ± 3 |
| 18 | 94.0 ± 2 | 93.0 ± 3.7 |
| 19 | 110 ± 12 | 94.3 ± 3.1 |
| 20 | 97.0 ± 24 | 95.0 ± 1.4 |
| 21 | 123 ± 5 | 100 ± 5 |
| 23 | 101 ± 0.5 | 97.8 ± 5 |
| 24 | 82.0 ± 7 | |
| 25 | 98.0 ± 7 | 95.3 ± 2 |
| 26 | 101 ± 11 | 100.3 ± 1.2 |

B. Signal Transduction

A variety of signal transduction pathways have been investigated in an effort to establish a concordance between particular pathways and the process of tumor promotion and development. Receptor-mediated transmembrane signaling utilizes effector enzymes such as phospholipase C (to produce inositol phosphates) and phospholipase $A_2$ (to release arachidonic acid). These same receptors and other membrane bound receptors can activate kinase enzymes directly or stimulate ion flux across the membrane. The effects of selected compounds on phosphatidyl inositol metabolism, arachidonic acid release, and $Ca^{2+}$ influx have now been examined.

Example 4

Phosphatidyl Inositol (H) Metabolism

This example illustrates the effect of compound 1 on the generation and release of phosphatidyl inositol from either A2058 cells (stimulated with autocrine motility factor) or CHOm5 cells (stimulated with carbachol).

Figure 7:
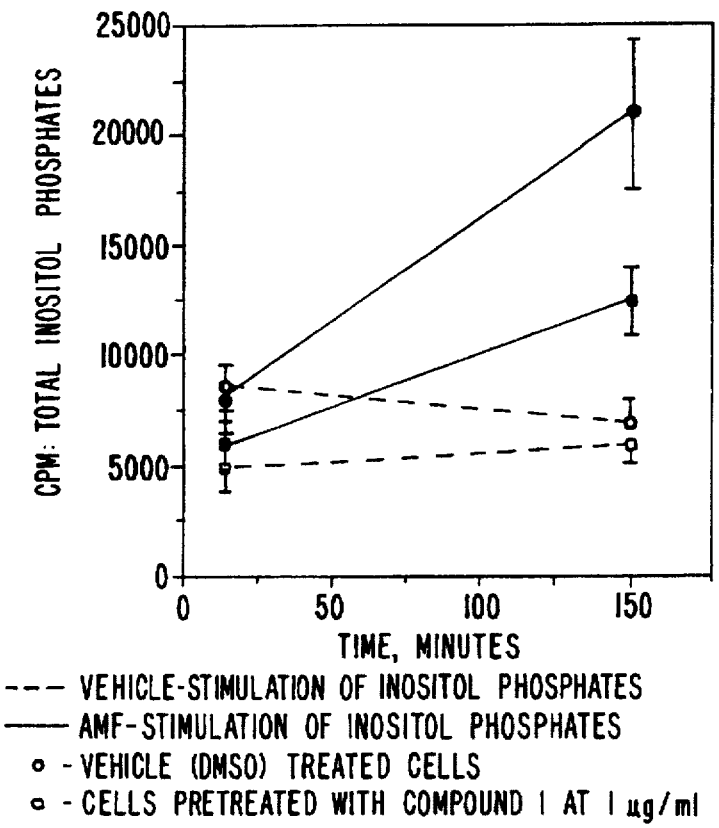
FIG. 7 shows the effect of 1 on AMF-stimulated generation of total inositol phosphates.

A2058 cells were incubated with compound 1 (1.0 µg/mL) for 24 hr, then labelled overnight with [$^3$H]inositol in serum-free, low inositol IMEM (LI-IMEM). Cells were then harvested, suspended, and incubated in LI-IMEM containing 10 mM LiCl for 30 min. The metabolism assay was initiated by the addition of either AMF or serum-free medium control to aliquots of 100,000 cells. The aliquots were incubated at 37° C. for 15 and 120 min, then washed twice with ice-cold PBS and extracted with chloroform-:methanol (1:2). The total inositol phosphates were removed using Dowex anion exchange column chromatography eluted with ammonium formate 1.0M/formic acid 0.1M buffer. Total inositol phosphates and unincorporated total intracellular [$^3$H]inositol were quantitated by ligand scintillation counting. Data are expressed as a ratio of total inositol phosphates to total unincorporated [$^3$H]inositol. As FIG. 7 indicates, compound 1 significantly inhibited AMF-stimulated phosphatidyl inositol hydrolysis. The degree of inhibition is similar to the inhibition of motility at the same dose (45%). Additionally, compound 1 had no appreciable effect on treated, unstimulated cells.

A second assay utilized CHO cells which were transfected with and stably expressed the m5 subtype of the muscarinic acetylcholine receptor.

CHOm5 cells were incubated with [$^3$H]inositol (0.5 µCi/well) for 18 to 24 hr. Before the addition of test compounds, the cells were washed twice with 250 µL of serum-free media supplemented with 20 mM HEPES and 10 mM lithium chloride. The test compounds were added in a final volume of 250 µL and the reaction was allowed to proceed for 15 min at 37° C. The reaction was stopped by the addition of 250 µL of an ice-cold solution containing 1M KOH, 18 mM $Na_2B_4O_7$, 3.8 mM EDTA and 7.6 mM NaOH. The stop solution was neutralized immediately with the addition of 250 µL of a solution containing 7.5% HCl. Released inositol phosphates were separated by anion exchange chromatography.

Figure 8:
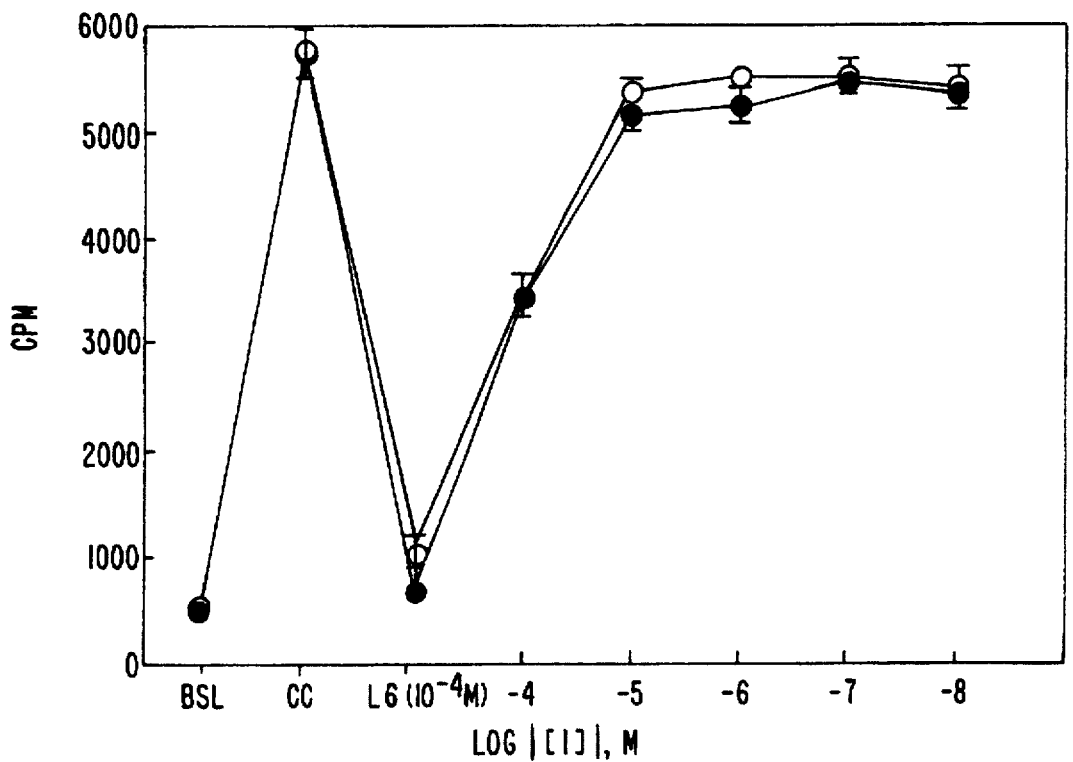
FIG. 8 shows the effect of 1 on inositol phosphate generation in carbachol-stimulated CHOm5 cells.

At concentrations above 10 µM, compound 1 partially inhibited carbachol-stimulated generation of inositol phosphates (FIG. 8).

Example 5

Arachidonic Acid Release

This example illustrates the effect of selected compounds on the release of arachidonic acid from carbachol-stimulated CHOm5 cells. Carbachol is a muscarinic agonist which in the muscarinic receptor transfected CHO cells stimulates the activation of phospholipase A2, resulting in arachidonic acid release and metabolism. Downstream metabolites of arachidonic acid, prostaglandins and leukotrienes are also second messengers.

Figure 9:
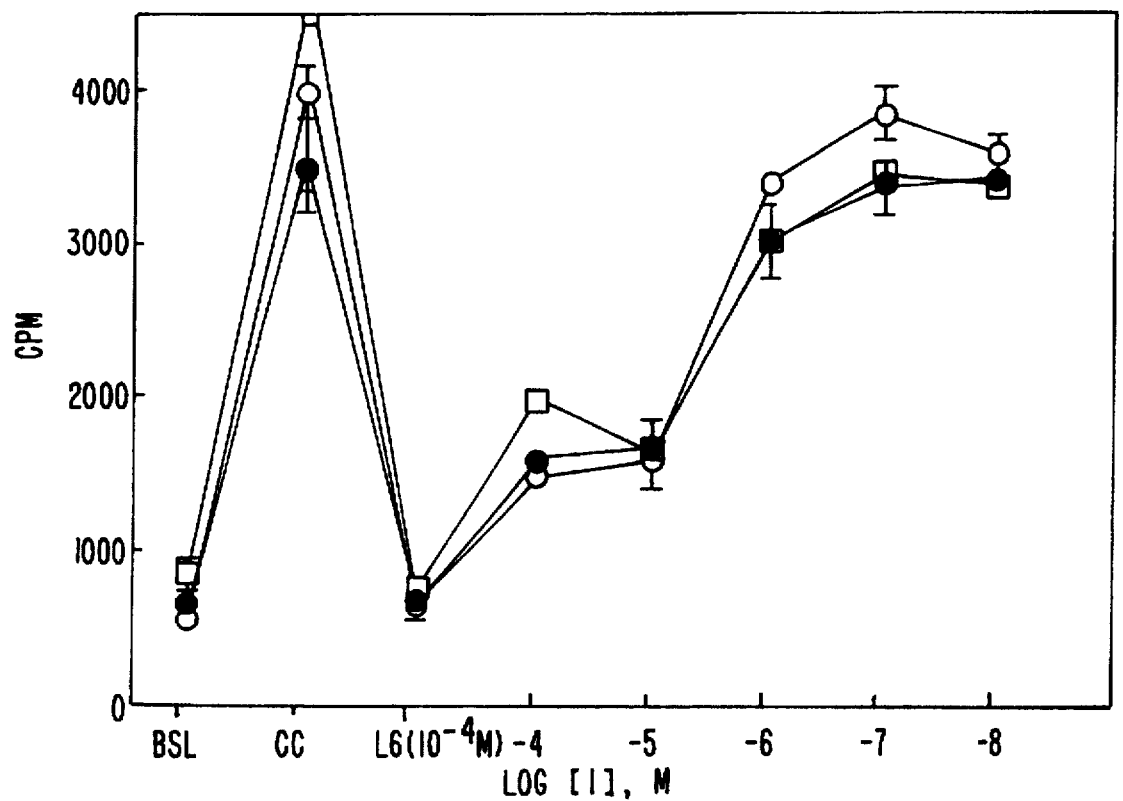
FIG. 9 shows the effect of 1 on arachidonic acid release from carbachol-stimulated CHOm5 cells.

The effect of compound 1 on arachidonic acid release from CHOm5 cells was determined by incubating the cells to isotopic equilibrium with labelled arachidonic acid, then washing the cells twice with 1 mL of serum-free media supplemented with 20 mM HEPES and 0.2% bovine serum albumin (fatty acid free) to trap the unincorporated labelled arachidonic acid, and then simultaneously adding carbachol (100 µM) and increasing concentrations of 1. After 15 min, the reaction was stopped by removing the incubation media which was then centrifuged at 10,000× g to eliminate any non-adherent cells. An aliquot of the supernatent was counted for released [$^3$H]arachidonic acid (see FIG. 9) in a liquid scintillation spectrophotometer and an $IC_{50}$ for compound 1 was determined ($IC_{50}$=5.2±0.8 nM).

Figure 10A:
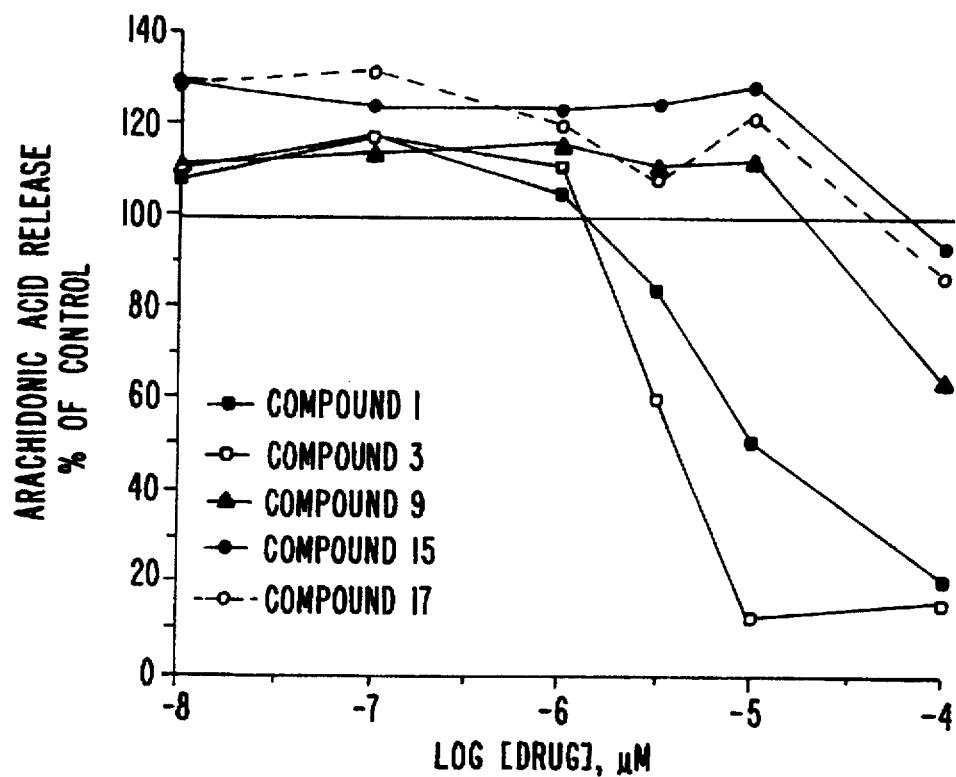
FIG. 10A shows the dose-dependent inhibition of arachidonic acid release by 1 and related compounds.
Figure 10B:
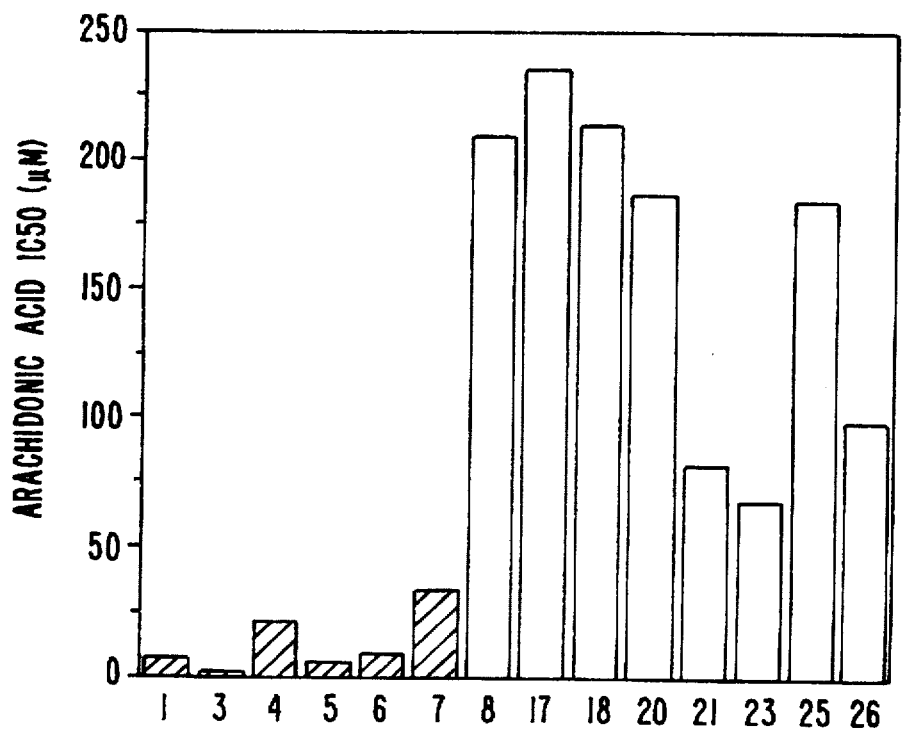
FIG. 10B shows the $IC_{50}$ concentrations for arachidonic acid release for selected compounds.

Compounds 1 and 3–6 inhibited the carbachol-stimulated release of arachidonic acid (Table I, FIG. 10). FIG. 11 shows the concentrations of selected test compounds necessary to achieve 50% inhibition of arachidonic acid release. Compounds not shown, but listed in Table I had projected $IC_{50}$ values greater than 250 µM.

Example 6

$Ca^{2+}$ Influx

This example illustrates the effect of selected compounds on calcium influx into either CHOm5 cells or A2058 cells.

Calcium influx was determined using two methods. The first method involved the use of $^{45}Ca_2$+, while the second method utilized a fluorescent intracellular calcium chelator, Fura-2. The method using Fura-2 is semi-quantitative and is preferred for kinetic analysis and screening whereas the $^{45}Ca^{2+}$ method is quantitative.

Figure 12:
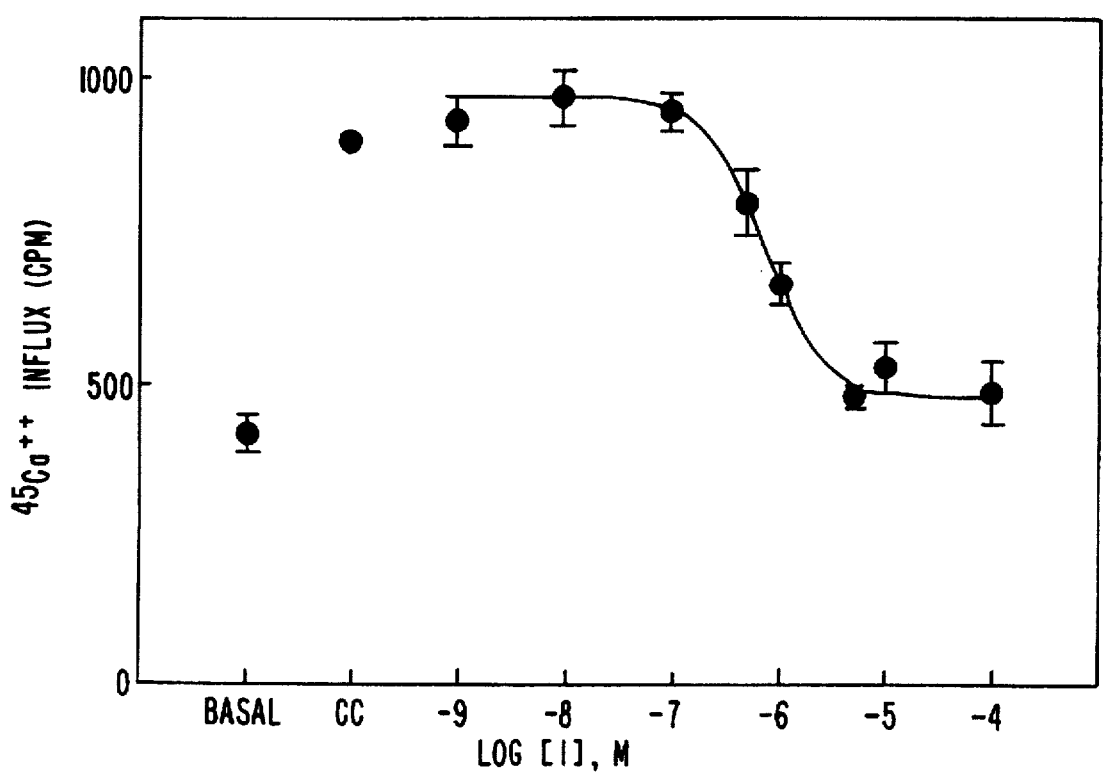
FIG. 12 shows the inhibition of carbachol-stimulated $^{45}Ca^{2+}$ influx in CHOm5 cells by 1. $IC_{50}$=935±18 nM.
Figure 13:
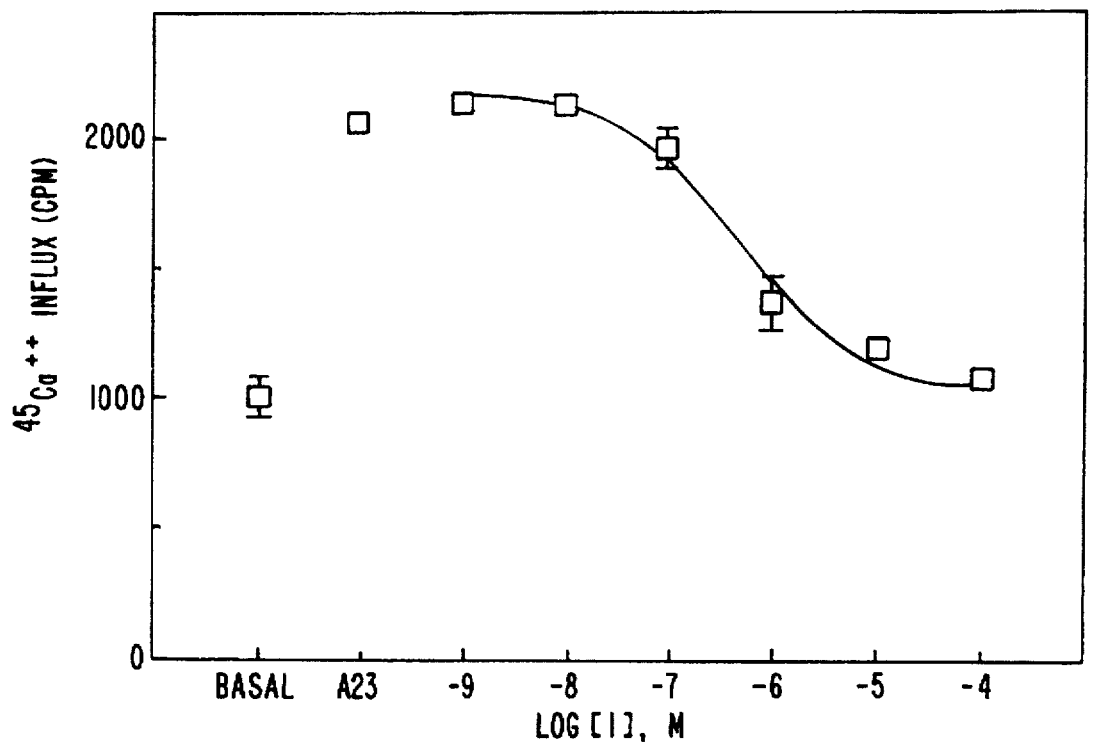
FIG. 13 shows the inhibition of calcium ionophore A23187-stimulated $^{45}Ca^{2+}$ influx in CHOm5 cells by compound 1 ($IC_{50}$=359±11 nN).

CHOm5 cells in monolayer culture were washed free of serum-containing media and incubated with either carbachol or the calcium ionophore A23187 (from Molecular Probes, Eugene, Oreg., USA) in the presence of $^{45}Ca^{2+}$ and defined buffer (E2 medium with 0.1 mM $MgCl_2$ and 1.0 mM $CaCl_2$). After incubation for 5 min, the radioactive buffer was rapidly and repeatedly washed off with media containing $LaCl_3$, a competitor of calcium efflux. The cell monolayer was solubilized and the calcium uptake was determined by scintillation counting. Results are shown in FIGS. 12 and 13.

Additionally, CHOm5 cells and A2058-1F5 human melanoma cells adherent to glass coverslips, which had been precoated with collagen or poly-L lysine to promote adhesion, were loaded with the fluorescent intracellular calcium chelator, fura-2AM. This chelator penetrates cells where it is hydrolyzed to fura-2 which remains trapped in the cells. Excess fura-2AM is washed off the cells. Cells are studied in serum-free E2 media, containing known amounts of calcium and magnesium. The cells are subjected to treatment with carbachol (10 µM) with or without compounds 1 and 2, and with appropriate vehicle controls (DMSO or PEG-400) in a perifusion apparatus. This ligand is known to stimulate intracellular release of calcium and influx of extracellular calcium. Emitted light is measured at 510 nm after excitation at 340 and 380 nm, with the ratio of fluorescence of fura-2 being directly correlated with intracellular calcium concentrations.

Figure 11A:
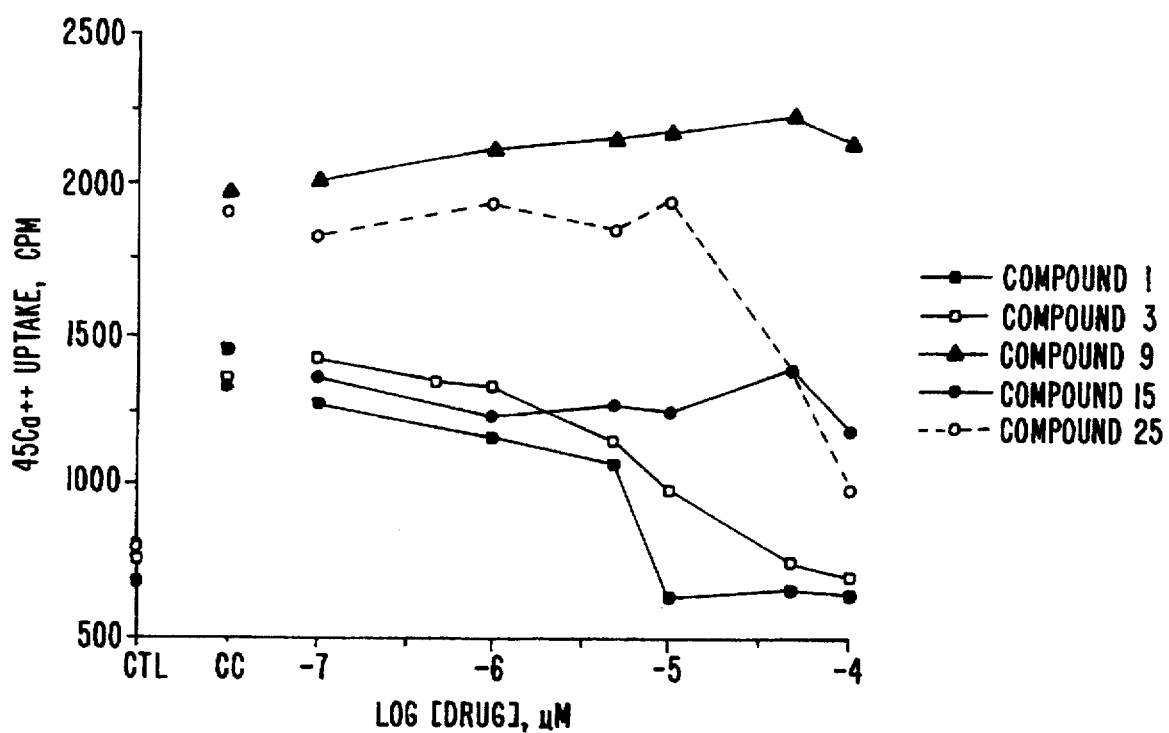
FIG. 11A shows the dose-dependent inhibition of $^{45}Ca^{2+}$ influx by compounds 1, 3, 9, 15, and 25.
Figure 11B:
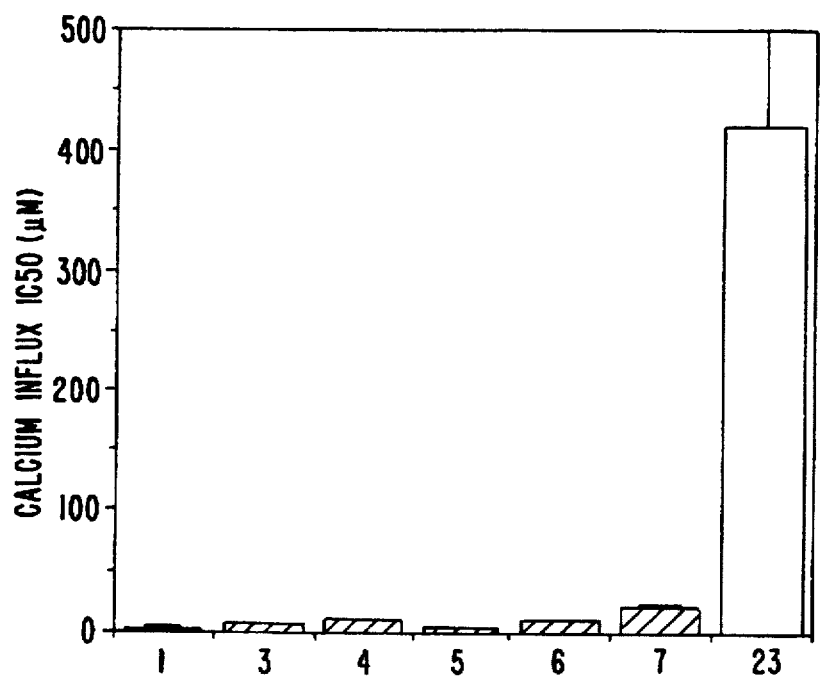
FIG. 11B shows $IC_{50}$ concentrations for $^{45}Ca^{2+}$ influx. Compounds not shown, but listed in Tables A–D had projected $IC_{50}$ values greater than 400 µM.

Compounds 1 and 3–6 were found to inhibit carbachol-stimulated $45Ca^{2+}$ uptake (see Table I). Similarly, treatment of the A2058 cells with these compounds also inhibited receptor-operated calcium flux (Table I). Compound 8, which is similar to compound 1 but which lacks the chloro substituents on the aromatic rings, failed to inhibit stimulated changes in intracellular calcium. FIGS. 11A and 11B provide the dose response results and $IC_{50}$ values for inhibition of receptor-operated $45Ca^{2+}$ influx. Stimulated uptake of radiolabelled calcium was measured as described above. The abbreviations CTL and CC are control and carbachol-stimulated calcium influx values, respectively.

TABLE I

The Effect of Selected Compounds on Calcium Influx

| Compounds | Inhibition of $Ca^{2+}$ Influx into A2058 Cells | % Inhibition of $^{45}Ca^{2+}$ Influx into CHOm5 Cells |
|---|---|---|
| 1 | + | 74 |
| 3 | + | 60 |
| 4 | + | 41 |
| 5 | + | 61 |
| 6 | + | 38 |
| 8 | − | 0 |
| 15 |  | 0 |
| 26 |  | −10 |

C. In vivo tests

The utility of inhibition of signal transduction as a new approach to cancer therapy requires that these in vitro effects translate to efficacy in vivo. Tests were developed to assess the efficacy of the test compounds in mice and humans, including treatment of tumor cells in vitro followed by injection (mouse), intraperitoneal injection of test compounds to hosts (mouse) and oral treatment of hosts bearing tumor cells (mouse and human).

Example 7

Preincubation of Tumor Cells with Test Compounds

This example illustrates the effect of selected compounds on the development of experimental pulmonary metastases, when the tumor cells are first incubated with the compound in vitro and subsequently injected into the tail vein of nude mice. In this example, both the 5R ras-transfected rat embryo fibroblast cell line and the HT-29 human colon cancer cell line were evaluated.

The 5R ras-transfected rat embryo fibroblast cell line forms confluent pulmonary metastases within 2-3 weeks after inoculation. For the experimental metastasis assay, 5R cells were treated in culture overnight with the test compounds (1-10 µM). After culture, the cells were harvested, washed and injected into the tail vein of six-week old nude mice. After 10 d, the mice were humanely sacrificed and the lungs were removed and fixed in Bouin's solution. The visible pulmonary metastases were counted. Compound 1 was found to inhibit pulmonary colonization by 95%, however the dehalogenated compound 8 only produced a 14% inhibition of colonization.

Figure 14:
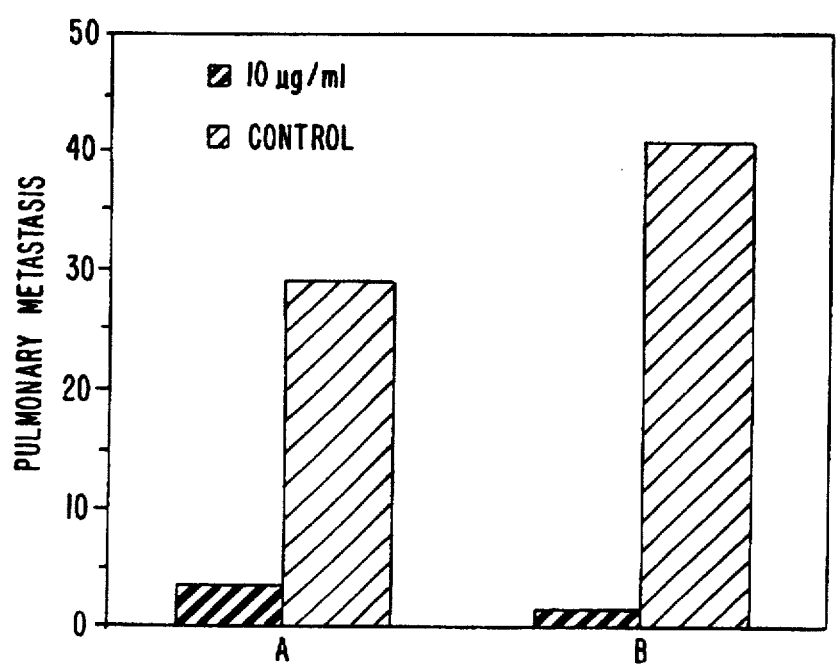
FIG. 14 shows that experimental pulmonary metastases due to human colon carcinoma are decreased in number and size by tumor cell treatment with 1.

Compound 1 was also tested for efficacy against HT-29 human colon cancer cells. HT-29 tumor cells were incubated with compound 1, 10 µg/mL, or DMSO vehicle (0.05%) for 24 hr. After harvesting and washing, one million cells were injected into the lateral tail vein of nude mice. Animals were humanely sacrificed on day 28, the lungs were inflated and fixed, and the number of pulmonary metastases were then counted. Observations on the size of the metastases were also made. As shown in FIG. 14, pretreatment of HT-29 cells with 1, resulted in a 96% inhibition of pulmonary colonization, and marked reduction in size.

Example 8

Intraperitoneal Injection of Mice

This example illustrates the effect of compound 1 on the survival of nude mice. The mice had been intraperitoneally injected with OVCAR3 human ovarian cancer cells followed, after three weeks, by intraperitoneal injection of 1.

The OVCAR3 human ovarian cancer animal model accurately approximates the clinical presentation of stage III-IV ovarian cancer of peritoneal carcinomatosis. Untreated, OVCAR3 tumor is lethal to nude mice.

Figure 15:
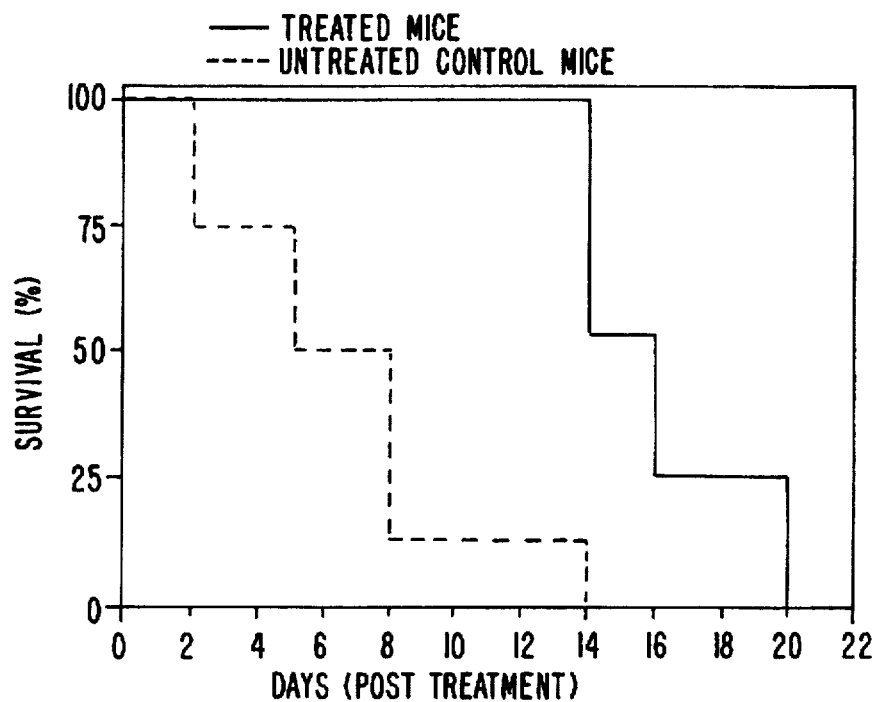
FIG. 15 shows the increased survival of nude mice bearing metastatic human ovarian carcinoma following treatment with 50 mg/kg/d of 1.

Six-week-old nude mice were inoculated intraperitoneally with $3.4 \times 10^-$ OVCAR3 human ovarian cancer cells. After a three week period, all animals had grossly distended abdomens due to OVCAR3 ascites. Two groups of animals (four each) were paired for relative severity of ascites and treatment was initiated. Compound 1.50 mg/kg/d in 60% DMSO (200 µL aliquot) or a vehicle alone, was administered via daily intraperitoneal injection. Overall survival from start of treatment was the study endpoint. Relative survival improvement was calculated as mean treatment group survival divided by mean control group survival. As shown in FIG. 15, overall survival was prolonged from 7.25±4.4 days to 16.0±2.5 days, an increase of 220%.

Example 9

Oral Administration of Test Compounds (Mouse)

This example illustrates the antitumor effect of compound 1 when administered orally to mice, following either subcutaneous inoculation of the mice with A2058 cells at two flank sites, intraperitoneal injection of OVCAR3 cells, or tail vein inoculation with 5R cells.

Figure 16A:
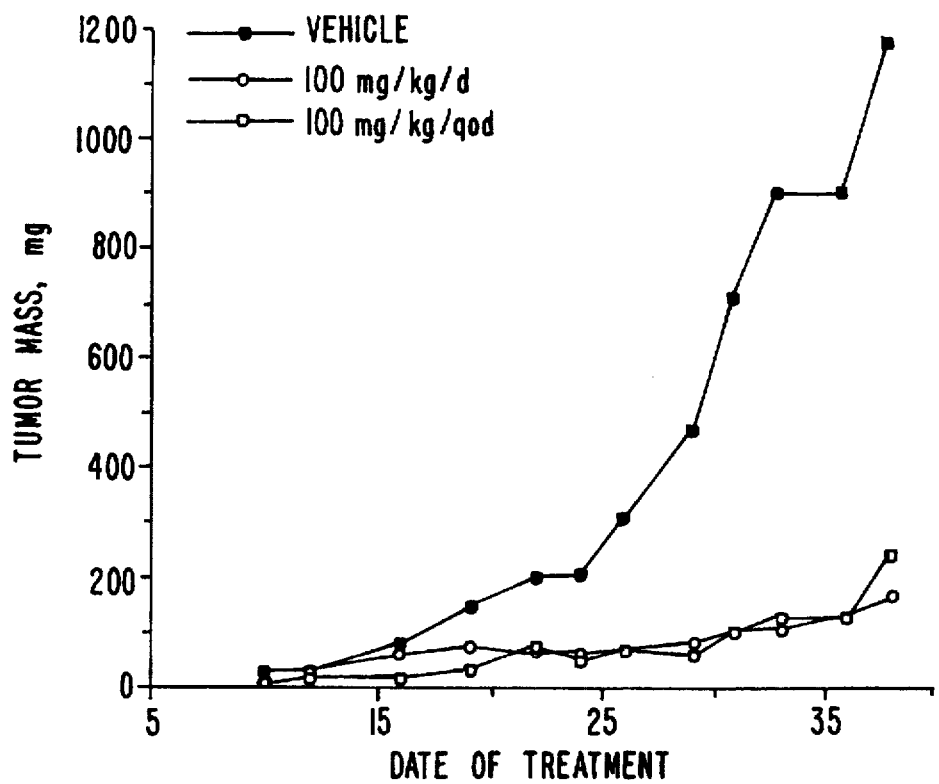
FIG. 16 shows the evaluation of oral administration of 1 to nude mice bearing human cancer xenografts. A. Average tumor mass (length×[width]$^2$) of A2058 human melanoma tumors determined serially in cohort of 10 mice per group inoculated at 2 sites per mouse. This experiment is representative of n=3 with 10 mice/group bearing duplicate inoculations. Tumor-free sites were not included in the average of tumor mass to prevent bias. B. Compound 1 treatment inhibits progression of OVCAR3 xenografts in nude mice. This experiment is representative of n=3 with 10 mice per group. Compound 1, 100 mg/kg or vehicle were administered by gavage in 100 µl aliquots. Total body weight was used as a surrogate marker of tumor burden for these animals bearing large intraperitoneal masses and malignant ascites.

The antitumor effect of compound 1 was tested on groups of 10 nude mice which had been inoculated subcutaneously at two flank sites with $10^6$ A2058 cells. Measureable tumors were observed within 14 days. On day 3 following tumor introduction, compound 1, diluted in PEG-400, or PEG-400 vehicle alone, was administered by gavage. Animals were monitored daily for toxicity, behavior, and extent of tumor. Weights and bidirectional measurements of a2058 tumor masses were determined three times per week. Significant growth arrest as well as a marked delay in tumor incidence was found (FIG. 16A). Marked necrosis in tumors from animals treated with 1 was seen at histologic evaluation of necropsy specimens. No gross toxicity was observed during the 35 days of compound 1 administration or at necropsy and histologic review of major organs.

Figure 16B:
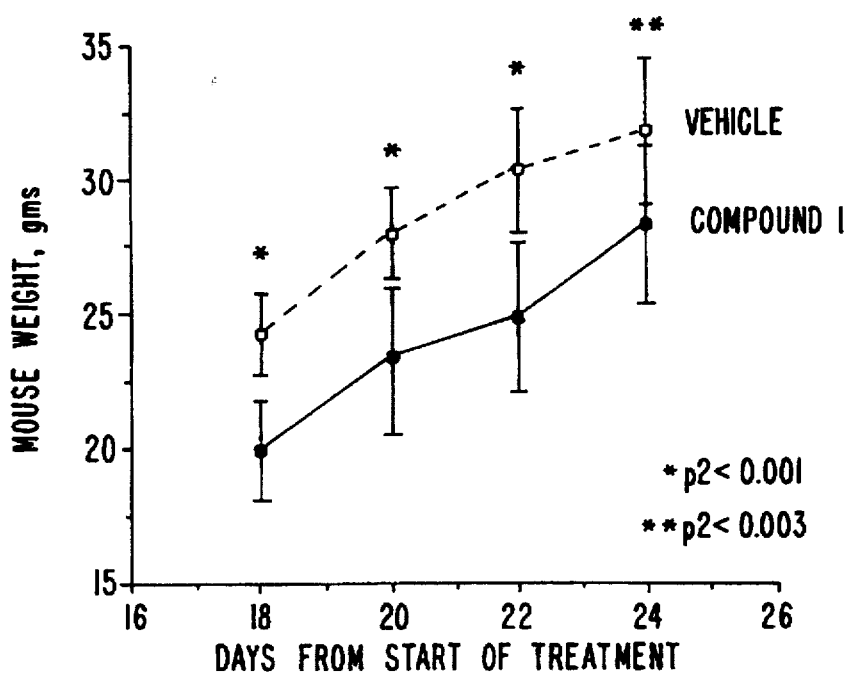

In a similar test, compound 1 was evaluated for treatment of nude mice which had been inoculated intraperitoneally with 30 million OVCAR3 cells. A daily oral administration of compound 1, (100 mg/kg, or PEG-400 vehicle) was started three days after inoculation. Statistically significant differences were seen in the time to development of ascites, body weight as a marker of total body tumor burden, and volume of ascites at necropsy (see also FIG. 16B). Histology of necropsy specimens showed compound 1 induced tumor necrosis and inhibition of pulmonary micrometastases.

Figure 17:
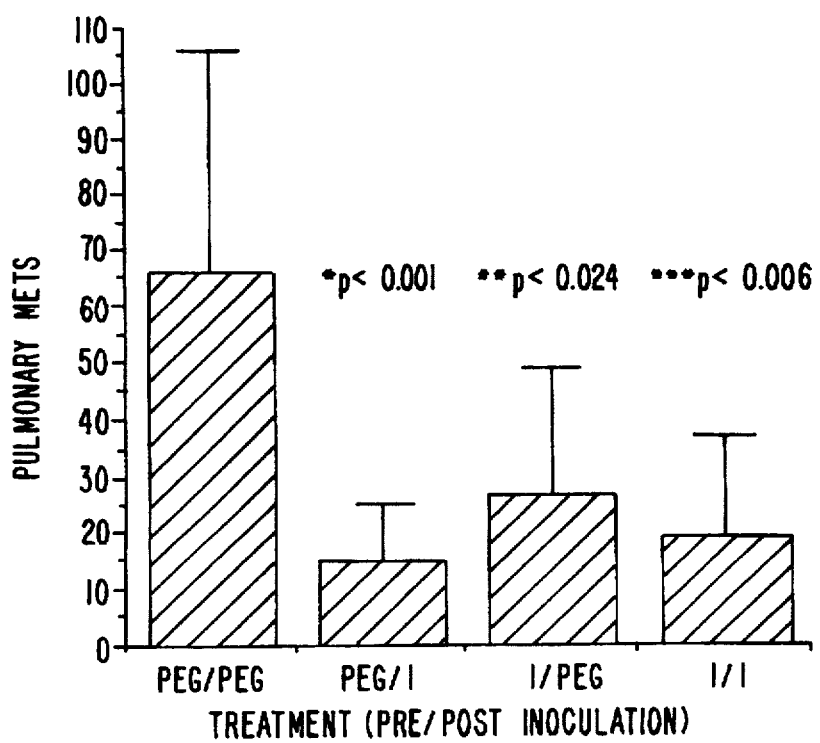
FIG. 17 shows that treatment with 1 prevents experimental metastasis. The number of pulmonary metastases due to 5R cells were statistically significantly inhibited by treatment with 1 prior to inoculation, post inoculation, and by continuous daily treatment prior to and post.

Finally, compound 1 was tested for efficacy in prevention of the formation and growth of experimental metastases. Oral administration of compound 1 or PEG-400 vehicle to nude mice was carded out for 5 days. On day 6, untreated 5R cells ($10^4$) were introduced into the animals by tail vein inoculation. The animals were then randomized into four groups. Two groups of animals which had received only vehicle were subsequently treated with either vehicle (PEG/PEG) or 1 (PEG/1). The other two groups which had been treated with 1 were similarly treated post-inoculation with either vehicle (1/PEG) or 1 (1/1). Treatments were continued for 10 d, after which the lungs were removed and the pulmonary metastases were counted. Histologic confirmation of the fibrosarcoma due to the 5R cells was obtained. As FIG. 17 indicates, compound 1 given prior to tumor cell injection prevented metastatic colonization as effectively as when 1 was administered only after tumor cell inoculation or when given continuously. No toxicity was noted during treatment or at necropsy.

Example 10

Oral Administration of Test Compound (Human)

This example illustrates the effect of compound 1 on tumor growth and metastasis when administered orally to seven patients in an FDA approved phase I clinical study.

Seven patients with solid tumor metastasis are undergoing treatment via oral administration of compound 1 under the FDA approved phase I clinical study. Table J provides data on the patients' response to this treatment. PT# is patient number. Response is the sum of the products of bidirectional measurements. No measurement means that while the disease was evaluable, it was not measureable. The concentration of the drug in the blood of the patients is well within the range which inhibits signal transduction in vitro and which inhibits tumor growth in vitro and in animals.

TABLE J

Types of Cancer, Sites of Metastatic Disease, Dose, Plasma Levels and Response in the Patients in Phase I Clinical Study

| PT# | PRIMARY DIAGNOSIS | SITES OF METASTATIC DISEASE | DOSE mg/m$^2$ | PEAK LEVEL μg/mL | RESPONSE |
|---|---|---|---|---|---|
| 1 | Melanoma | Lung | 100 qod | 1.25 | Stable (+8%) |
| 2 | Colon | Retroperitoneal lymph nodes | 100 qd | 3.61 | Stable (−22%) |
| 3 | Colon | Lung, Liver | 100 qd | 3.53 | Stable |
| 4 | Ovary | Retroperitoneal lymph nodes | 100 qd | 3.08 | Stable (−21%) |
| 5 | Lung | Lung | 200 qod | 1.77 | Stable |
| 6 | Carcinoid | Lung, Liver | 200 qod | 1.34 | Stable |
| 7 | Colon | Lung, Liver | 200 qod | 2.83 | Progression |

In the first patient, significant inhibition of the growth rate for two out of two melanoma lung metastases was observed by X-ray measurement.

Metastasis lesion #1: 79% inhibition of growth rate (cm$^2$/day)

Metastasis lesion #2: 59% inhibition of growth rate (cm$^2$/day)

Figure 18:
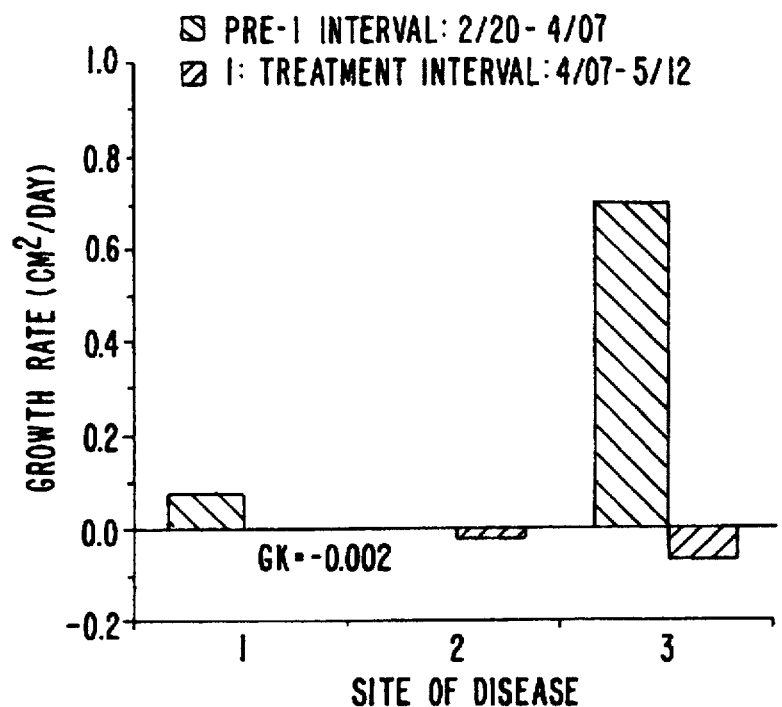
FIG. 18 shows the suppression and regression of 3 of 3 colon cancer metastasis in patient number two.

The second patient had suppression and regression of 3 of 3 colon cancer metastases (see FIG. 18).

Additionally, the side effects in the humans to date do not show any bone marrow depression (no reduction in white cell counts), do not show any liver or kidney function abnormalities, no neurological toxicity, hair loss or electrolyte imbalances. Furthermore, no abnormalities of blood cellular composition are found in humans to date when compound 1 is administered orally. Side effects found using standard cytotoxic chemotherapy typically includes gastrointestinal lining cell sloughing, depression of white blood cell count, depression of red blood cell count, depression of platelet count, hair loss, kidney and liver function changes, and neuropathy. The total absence of these side effects under the current treatment protocol is consistent with the mechanism of action of 1 residing in a novel site, the blockage of signal transduction.

Example 11

Determination of Circulating Plasma Concentrations of Compound 1

This example demonstrates the levels of compound 1 in blood plasma which are achieved over periods of time following administration of the compound. This example also demonstrates that sufficient levels of 1 are available to provide a therapeutic response in humans.

Murine data: A cohort of nude mice were inoculated with A2058 cells and treated with compound 1 at rates of 100 mg/kg/d and 250 mg/kg/qod. These animals were sacrificed humanely at 4 day intervals beginning 18 hr after oral administration of 1. Plasma was collected and frozen until evaluation by HPLC. Plasma samples were precipitated with 10% trichloroacetic acid and extracted with methylene chloride. The organic extract was evaporated to dryness under a stream of nitrogen, reconstituted and chromatographed by HPLC using an isocratic elution of 70% methanol in 0.1M ammonium acetate (pH 6.5) on a C-18 analytical column. The lower level of sensitivity of this method is 20 ng/mL. The levels of compound 1 in plasma ranged from 1–5 μg/mL in the 100 mg/kg/d cohort and from 5–10 μg/mL in the 250 mg/kg/qod group. These plasma levels are in the range determined to be biologically significant in the inhibition of signal transduction.

Figure 19:
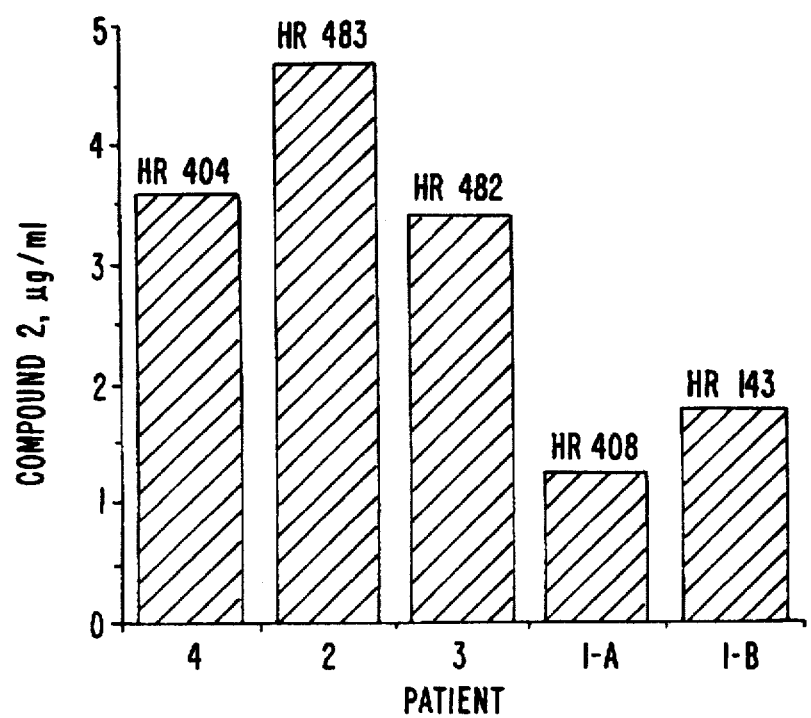
FIG. 19 shows the peak/steady levels of 1 for four patients enrolled in the phase I clinical study.

Human data: FIG. 19 shows peak/steady state levels for four patients enrolled in the phase I clinical trial. The concentration of compound 1 in the blood of patient #1 was from 1–2 μg/mL, while that of the other three patients was >3 μg/mL (>7 μM). These concentrations are well within the range which inhibit signal transduction in vitro and which inhibit tumor growth in animals. Evaluation of the murine plasma levels and the human plasma levels as shown in FIG. 19 demonstrates the equivalence of the murine and human data.

D. Correlation Studies

Example 12

This example provides a correlation between the effect which selected compounds have on receptor-stimulated arachidonic acid release and calcium influx. This example also illustrates the relationship of calcium influx as a function of tumor cell growth and further provides a correlation between signal transduction and tumor growth.

Figure 21A:
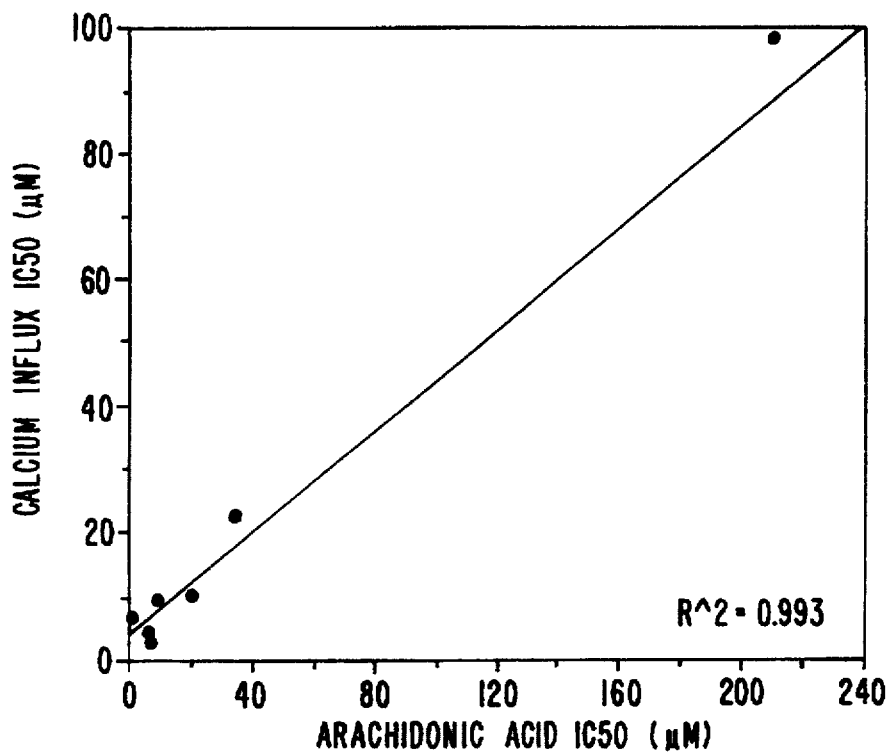
FIG. 21 demonstrates a direct relationship between inhibition of arachidonic acid release and calcium uptake (A) and inhibition of calcium influx and proliferation (B).
Figure 21B:
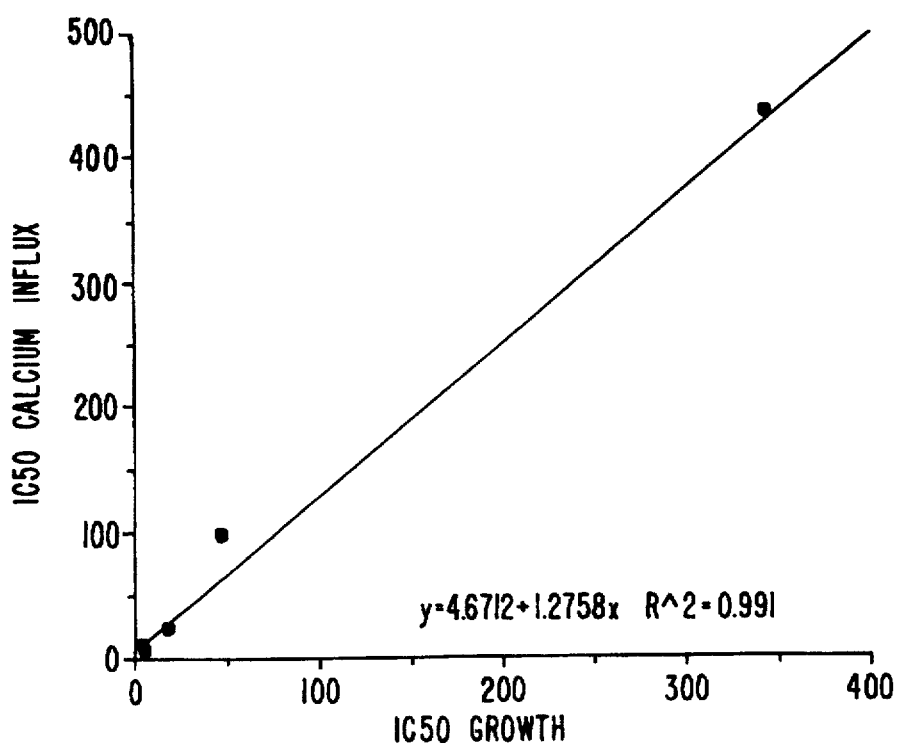

Others have suggested that muscarinic receptor-operated calcium influx was necessary for muscarinic receptor-induced arachidonic acid release (Felder, et al., *J. Pharmacol. Exp. Ther.*, 255:1140–1147 (1990)). Compounds 1 and those with $IC_{50}$ levels ≦240 μM demonstrated a significant equivalence of effectiveness against arachidonic acid release and calcium influx (see FIG. 21A, linear regression coefficient $r^2=0.993$). The effective concentrations of each compound was lower for inhibition of calcium influx than for arachidonic acid release, linking receptor-stimulated calcium influx with arachidonic acid release. A further relationship was discovered when the $IC_{50}$ values for calcium influx and growth inhibition of the compounds were evaluated (FIG. 21B, linear regression coefficient $r^2=0.991$). These data strongly suggest that the inhibition of calcium influx is causatively linked with the inhibition of proliferation and colony formation.

A correlation between signal transduction and tumor growth was demonstrated for compounds 1 and 3–26. Table K shows the results of several assays for representative compounds. Compound 1 was inhibitory for the biological and biochemical assays. Compounds 3–7 were similarly inhibitory for all systems tested. In contrast, compound 8 (a dehalogenated analog of 1) did not inhibit any of the test assays. Compounds 9–26 also failed to provide any significant inhibition in any of the test assays.

TABLE K

Correlation of Signal Transduction Assays With Colony Formation and Cell Growth for Selected Compounds

| Compound | Inhibition of Calcium Influx | Arachidonic Acid Release (% of Control) | Colony Formation (% of Control) | Growth (% of Control) |
|---|---|---|---|---|
| 1 | + | 50.9 ± 9 | 11.1 ± 5 | 36.4 ± 6 |
| 3 | + | 13.1 ± 3 | 10.2 ± 0.5 | 31.5 ± 7 |
| 4 | + | 73.8 ± 5.9 | 10.3 ± 0.4 | 53.7 ± 15 |
| 5 | + | 49.2 ± 12 | 9.97 ± 1 | 39.0 ± 2 |
| 6 | + | 49.6 ± 5 | 9.00 ± 1 | 45.3 ± 11 |
| 7 | + | 92.6 ± 7 | — | 66.5 ± 9 |
| 8 | − | 100 ± 15 | 93.4 ± 3 | 92.7 ± 9 |

The invention being thus described, it will be obvious that the same may be varied in many ways. Such variations are not to be regarded as a departure from the spirit and scope of the invention, and all such modification as would be obvious to one skilled in the an are intended to be included within the scope of the following claims.

What is claimed is:

1. A method of inhibiting the invasion and metastasis of malignant solid tumors in mammals, said method comprising administering to said mammal an anti-proliferative, anti-invasive and anti-metastasis effective amount of a compound selected from the group of formulas consisting of:

and

wherein:

p is an integer of from 0 to 4;

$Ar^1$ is a moiety selected from the group consisting of —$Ar^2$—X—$Ar^3$, phenyl, trioxaadamantyl, anthracenyl, anthraquinonyl, naphthyl, phenanthryl, and substituted versions thereof;

$Ar^2$ and $Ar^3$ are each aromatic moieties independently selected from the group consisting of phenyl, naphthyl, and substituted versions thereof;

X is a linking moiety selected from the group consisting of O, S, $SO_2$, CO, CHCN, straight chain alkyl, alkoxy, and alkoxyalkyl; and Z is a nitrogen-containing heterocyclic moiety selected from the group consisting of imidazolyl, 1,2,3-triazolyl, 1,2,4-triazolyl and substituted versions thereof, said heterocyclic moiety being attached to the —$(CH_2)_p$— portion of the molecule at the N1 position of the heterocycle.

2. A method in accordance with claim 1 wherein said compound is of formula (I).

3. A method in accordance with claim 1 wherein said compound is of formula (I), $Ar^1$ is —$Ar^2$—X—$Ar^3$, $Ar^2$ and $Ar^3$ are both substituted phenyl, and Z is a nitrogen-containing heterocyclic moiety selected from the group consisting of imidazolyl, 1,2,3-triazolyl, and substituted versions thereof.

4. A method in accordance with claim 1 wherein said compound is of formula (I), p is an integer of from 0 to 2, $Ar^1$ is —$Ar^2$—X—$Ar^3$, $Ar^2$ and $Ar^3$ are both substituted phenyl, and Z is a nitrogen-containing heterocyclic moiety selected from the group consisting of imidazolyl, and 1,2,3-triazolyl, and substituted versions thereof.

5. A method in accordance with claim 1 wherein said compound is of formula (I), p is an integer of from 0 to 2, $Ar^1$ is —$Ar^2$—X—$Ar^3$, $Ar^2$ and $Ar^3$ are both substituted phenyl, X is a linking moiety selected from the group consisting of O, CO, and CHCN, and Z is a nitrogen-containing heterocyclic moiety selected from the group consisting of imidazolyl, and 1,2,3-triazolyl, and substituted versions thereof.

6. A method in accordance with claim 1 wherein said compound is of formula (I), p is 1, $Ar^1$ is —$Ar^2$—X—$Ar^3$, $Ar^2$ and $Ar^3$ are both substituted phenyl, X is CO, and Z is a nitrogen-containing heterocyclic moiety selected from the group consisting of imidazolyl, and 1,2,3-triazolyl, and substituted versions thereof.

7. A method in accordance with claim 1 wherein said compound is of formula (I), p is 1, $Ar^1$ is —$Ar^2$—X—$Ar^3$, $Ar^2$ and $Ar^3$ are both substituted phenyl, X is CO, and Z is 5-amino-4-carboxamido-1,2,3-triazolyl.

8. A method in accordance with claim 1 wherein said compound is of formula (I), p is 1, $Ar^1$ is —$Ar^2$—X—$Ar^3$, $Ar^2$ is 2,6-dichlorophenyl, $Ar^3$ is 4-chlorophenyl, X is CO, and Z is 5-amino-4-carboxamido-1,2,3-triazolyl.

9. A method in accordance with claim 1 wherein said compound is of formula (I), $Ar^1$ is a moiety selected from the group consisting of trioxaadamantyl, anthracenyl, anthraquinonyl, naphthyl, and phenyl and substituted versions thereof, Z is a nitrogen-containing heterocyclic moiety selected from the group consisting of imidazolyl, 1,2,3-triazolyl, and substituted versions thereof.

10. A method in accordance with claim 1 wherein said compound is of formula (I), p is 1, $Ar^1$ is trioxaadamantyl, and Z is a nitrogen-containing heterocyclic moiety selected from the group consisting of imidazolyl, and 1,2,3-triazolyl, and substituted versions thereof.

11. A method in accordance with claim 1 wherein said compound is of formula (I), p is 1, $Ar^1$ is 10-chloro-9-anthracenyl, and Z is a nitrogen-containing heterocyclic moiety selected from the group consisting of imidazolyl, and 1,2,3-triazolyl, and substituted versions thereof.

12. A method in accordance with claim 1 wherein said compound is of formula (I), p is 1, $Ar^1$ is 2-anthraquinonyl, and Z is a nitrogen-containing heterocyclic moiety selected from the group consisting of imidazolyl, and 1,2,3-triazolyl, and substituted versions thereof.

13. A method in accordance with claim 1 wherein said compound is of formula (I), p is 1, $Ar^1$ is phenyl or substituted phenyl, and Z is a nitrogen-containing heterocyclic moiety selected from the group consisting of imidazolyl, and 1,2,3-triazolyl, and substituted versions thereof.

14. A method in accordance with claim 1 wherein said compound is of formula (I), p is 1, $Ar^1$ is naphthyl or substituted naphthyl, and Z is a nitrogen-containing heterocyclic moiety selected from the group consisting of imidazolyl, and 1,2,3-triazolyl, and substituted versions thereof.

* * * * *